(12) United States Patent
Ju et al.

(10) Patent No.: US 8,927,207 B2
(45) Date of Patent: Jan. 6, 2015

(54) MIRNAS AS THERAPEUTIC TARGETS IN CANCER

(75) Inventors: Jingfang Ju, East Setauket, NY (US); Bo Song, Dilian (CN); Yuan Wang, Wuhan (CN)

(73) Assignee: Research Foundation of State University of New York, Albany, NY (US)

( * ) Notice: Subject to any disclaimer, the term of this patent is extended or adjusted under 35 U.S.C. 154(b) by 45 days.

(21) Appl. No.: 12/996,249

(22) PCT Filed: Jun. 5, 2009

(86) PCT No.: PCT/US2009/046353
§ 371 (c)(1),
(2), (4) Date: Mar. 15, 2011

(87) PCT Pub. No.: WO2009/149318
PCT Pub. Date: Dec. 10, 2009

(65) Prior Publication Data
US 2011/0166201 A1    Jul. 7, 2011

Related U.S. Application Data

(60) Provisional application No. 61/122,377, filed on Dec. 13, 2008, provisional application No. 61/059,197, filed on Jun. 5, 2008.

(51) Int. Cl.
*C12Q 1/68* (2006.01)
*C12N 15/113* (2010.01)

(52) U.S. Cl.
CPC ........ *C12N 15/113* (2013.01); *C12N 2310/113* (2013.01); *C12N 2310/14* (2013.01); *C12N 2320/31* (2013.01)
USPC ............... 435/6; 435/325; 435/375; 536/24.5

(58) Field of Classification Search
None
See application file for complete search history.

(56) References Cited

U.S. PATENT DOCUMENTS

| | | | |
|---|---|---|---|
| 2005/0182005 A1* | 8/2005 | Tuschl et al. | 514/44 |
| 2005/0261218 A1* | 11/2005 | Esau et al. | 514/44 |
| 2005/0266418 A1 | 12/2005 | Chen et al. | |
| 2005/0272683 A1 | 12/2005 | Koropatnick et al. | |
| 2008/0050744 A1* | 2/2008 | Brown et al. | 435/6 |
| 2010/0267813 A1* | 10/2010 | Esau et al. | 514/44 R |
| 2010/0286385 A1* | 11/2010 | Tuschl et al. | 536/24.5 |

FOREIGN PATENT DOCUMENTS

WO    2005078139 A2    8/2005

OTHER PUBLICATIONS

Tang et al. (FASEB Journal 2007, vol. 21:3777-3785).*
Xi et al., "Prognostic Values of MicroRNAs in Colorectal Cancer", Biomarker Insights, (2006), vol. 1, pp. 113-121.
Calin et al., "MicroRNA-Cancer Connection: The Beginning of a New Tale", Cancer Res., (Aug. 1, 2006), vol. 66, No. 15, pp. 7390-7394.
Nakajima et al., "Non-coding MicroRNAs hsa-let-7g and hsa-miR-181b are Associated with Chemoresponse to S-1 in Colon Cancer", Cancer Genomics Proteomics, (Oct. 3, 2006), vol. 3, No. 5; pp. 317-324.
Calin et al., "A MicroRNA Signature Associated with Prognosis and Progression in Chronic Lymphocytic Leukemia", The New England Journal of Medicine, (Oct. 27, 2005), vol. 353, No. 17, pp. 1793-1801.
Schratt et al., "A brain-specific microRNA regulates dendritic spine development", Nature Publishing Group, (Jan. 19, 2006), vol. 439, No. 19, pp. 283-289.
Lau et al., "An Abundant Class of Tiny RNAs with Probable Regulatory Roles in Caenorhabditis elegans", Science, (Oct. 26, 2001), vol. 294, pp. 858-862.
Lee et al., "An Extensive Class of Small RNAs in Caenorhabditis elegans", Science, (Oct. 26, 2001), vol. 294, pp. 862-864.
Brennecke et al., "Bantam Encodes a Developmentally Regulated microRNA that Controls Cell Proliferation and Regulates the Proapoptotic Gene hid in Drosophila", Cell, (Apr. 4, 2003), vol. 113, pp. 25-36.
Arango et al., "c-myc/p53 Interaction Determines Sensitivity of Human Colon Carcinoma Cells to 5-Fluorouracil in Vitro and in Vivo", Cancer Research, (Jun. 15, 2001), vol. 61, pp. 4910-4915.
Salonga et al., "Colorectal Tumors Responding to 5-Fluorouracil Have Low Gene Expression Levels of Dihydropyrimidine Dehydrogenase, Thymidylate Synthase, and Thymidine Phosphorylase", Clinical Cancer Research, (Apr. 2000), vol. 6, pp. 1322-1327.
Akervall et al., "Cyclin D1 Overexpression versus Response to Induction Chemotherapy in Squamous Cell Carcinoma of the Head and Neck", Acta Oncologica, (2001), vol. 40, No. 4, pp. 505-511.

(Continued)

*Primary Examiner* — Kimberly Chong
(74) *Attorney, Agent, or Firm* — The Webb Law Firm

(57) ABSTRACT

MicroRNAs (miRNAs) are a class of non-coding small RNA molecules that regulate gene expression at the post-transcriptional level by interacting with 3' untranslated regions (UTRs) of their target mRNAs. The invention relates to the application of miR-192 and miR-215. Both of these miRNAs impact cellular proliferation through the p53-miRNA circuit, and interact with dihydrofolate reductase (DHFR) and thymidylate synthase (TS). Particularly, upregulation of these miRNAs reduces cellular proliferation. The invention relates to this discovery. For example, inhibiting miR-192 and/or miR-215 sensitizes a neoplasm or a subject with a neoplasm to chemotherapeutic agents. Furthermore, measuring the levels of miR-192 and/or miR-215 provides one with information regarding whether the neoplasm or subject will respond to chemotherapeutic agents. Accordingly, the invention relates to composition and methods relating to the identification, characterization and modulation of the expression of miR-192 and miR-215.

6 Claims, 27 Drawing Sheets

(56) References Cited

OTHER PUBLICATIONS

Xi et al., "Differentially Regulated Micro-RNAs and Actively Translated Messenger RNA Transcripts by Tumor Suppressor p53 in Colon Cancer", Clin. Cancer Res., (Apr. 1, 2006), vol. 12, No. 7, pp. 2014-2024.
Elliott et al., "E2F-1 Gene Therapy Induces Apoptosis and Increases Chemosensitivity in Human Pancreatic Carcinoma Cells", Tumor Biology, (2002), vol. 23, pp. 76-86.
Van Den Brande et al., "EORTC Early Clinical Studies Group early phase II trial of S-I in patients with advanced or metastatic colorectal cancer", British Journal of Cancer, (2003), vol. 88, pp. 648-653.
Heidelberger et al., "Fluorinated Pyrimidines, A New Class of Tumour-Inhibitory Compounds", Nature, (Mar. 30, 1957), No. 4561, pp. 663-666.
Lagos-Quintana et al., "Identification of Novel Genes Coding for Small Expressed RNAs", Science, (Oct. 26, 2001), vol. 294, pp. 853-858.
Lagos-Quintana et al., "Identification of Tissue-Specific MicroRNAs from Mouse", Current Biology, (Apr. 30, 2002), vol. 12, pp. 735-739.
Reinhart et al., "MicroRNAs in plants", Genes & Development, (2002), vol. 16, pp. 1616-1626.
Mourelatos et al., "miRNPs: a noval class of ribonucleoproteins containing numerous microRNAs", Genes & Development, (2002), vol. 16, pp. 720-728.
Lagos-Quintana et al., "New microRNAs from mouse and human", RNA, (2003), vol. 9, pp. 175-179.
Banerjee et al., "Novel aspects of resistance to drugs targeted to dihydrofolate reductase and thymidylate synthase", Biochimica et Biophysica Acta, (2002), vol. 1587, pp. 164-173.
Mcdermott et al., "Molecular and biochemical markers in colorectal cancer", European Society for Medical Oncology, (2002), 13 Suppl. 4, pp. 235-245.
Vallbohmer et al., "Molecular factors of 5-fluorouracil metabolism in colorectal cancer: Analysis of primary tumor and lymph node metastasis", International Journal of Oncology, (2006), vol. 28, pp. 527-533.
Ajani et al., "Multicenter Phase II Trial of S-1 Plus Cisplatin in Patients With Untreated Advanced Gastric or Gastroesophageal Junction Adenocarcinoma", Journal of Clinical Oncology, (Feb. 1, 2006), vol. 24, No. 4, pp. 663-667.
Klampfer et al., "Oncogenic Ras increases sensitivity of colon cancer cells to 5-FU-induced apoptosis", Oncogene (2005), vol. 24, pp. 3932-3941.
Klampfer et al., "Oncogenic Ras Promotes Butyrate-induced Apoptosis through Inhibition of Gelsolin Expression", The Journal of Biological Chemistry, (Aug. 27, 2004), vol. 279, No. 35, pp. 36680-36688.
Elsaleh et al., "p53 Gene Mutation, Microsatellite Instability and Adjuvant Chemotherapy: Impact on Survival of 388 Patients with Dukes' C Colon Carcinoma", Oncology, (2000), vol. 58, pp. 52-59.
Shirao et al., "Phase II Study of Oral S-1 for Treatment of Metastatic Colorectal Carcinoma", Cancer, (Jun. 1, 2004), vol. 100, No. 11, pp. 2533-2361.
Ohtsu et al., "Phase II study of S-1, a novel oral fluoropyrimidine derivative, in patients with metastatic colorectal carcinoma", British Journal of Cancer (2000), vol. 83, No. 2, pp. 141-145.
Johnson et al., "RAS Is Regulated by the let-7 MicroRNA Family", Cell, (Mar. 11, 2005), vol. 120, pp. 635-647.
Michael et al., "Reduced Accumulation of Specific MicroRNAs in Colorectal Neoplasis", Molecular Cancer Research, (Oct. 2003), vol. 1, pp. 882-891.
Reinhart et al., "The 21-nucleotide let-7 RNA regulates development timing in Caenorhabditis elegans", Nature, (Feb. 24, 2000), vol. 403, pp. 901-906.
Lee et al., "The C. elegans Heterochronic Gene lin-4 Encodes Small RNAs with Antisense Complementarity to Iin-14", Cell, (Dec. 3, 1993), vol. 75, pp. 843-854.

Xu et al., "The Drosophila MicroRNA Mir-14 Suppresses Cell Death and Is Required for Normal Fat Metabolism", Current Biology, (Apr. 29, 2003), vol. 13, pp. 790-795.
Schoffski, "The modulated oral fluoropyrimidine prodrug S-1, and its use in gastrointestinal cancer and other solid tumors", Anti-Cancer Drugs, (2004), vol. 15, No. 2, pp. 85-106.
Chen et al., "The role of microRNA-1 and microRNA-133 in skeletal muscle proliferation and differentiation", Nat. Genet., (Feb. 2006), vol. 38, No. 2, pp. 228-233.
Wang et al., "Analyses of p53 Target Genes in the Human Genome by Bioinformatic and Microarray Approaches", The Journal of Biological Chemistry, (Nov. 23, 2001), vol. 276, No. 47, pp. 43604-43610.
Krek et al., "Combinatorial microRNA target predictions", Nature Genetics, (May 2005), vol. 37, No. 5, pp. 495-500.
Bunz et al., "Disruption of p53 in human cancer cells alters the responses to therapeutic agents", The Journal of Clinical Investigation, (Aug. 1999), vol. 104, No. 3, pp. 263-269.
Yu et al., "Effect of p53 Status on Tumor Response to Antiangiogenic Therapy", Science (2002), vol. 295, pp. 1526-1528.
Calin et al., "Frequent deletions and down-regulation of micro-RNA genes miR15 and miR16 at 13q14 in chronic lymphocytic leukemia", PNAS, (Nov. 26, 2002), vol. 99, No. 24, pp. 15524-15529.
John et al., Human MicroRNA Targets, PLoS Biology, (Nov. 2004), vol. 2, Issue 11, pp. 1862-1879.
Bandres, et al., "Identification by Real-time PCR of 13 mature microRNAs differentially expressed in colorectal cancer and non-tumoral tissues", Molecular Cancer, (2006), vol. 5, No. 29, pp. 1476-4598.
Belvedere et al., "Lack of correlation between immunohistochemical expression of E2F-1, thymidylate synthase expression and clinical response to 5-fluorouracil in advanced colorectal cancer", Annals of Oncology, (2004), vol. 15, pp. 55-58.
Benard et al., "Micro-ARN et oncogenese", Bull Cancer, (2005), vol. 92, No. 9, pp. 757-762.
Wienholds et al., "MicroRNA function in animal development", FEBS Letters, (2005), vol. 579, pp. 5911-5922.
Chen et al., "microRNA-guided posttranscriptional gene regulation", Biol. Chem., (Dec. 2005), vol. 386, pp. 1205-1218.
Hammond, "MicroRNAs as oncogenes", Genetics & Development, (2006), vol. 16, pp. 4-9.
Hampton, "MicroRNAs Move Into Cancer Research", JAMA, (Jul. 27, 2005), vol. 294, No. 4, pp. 411-412.
Calin et al., "MicroRNA profiling reveals distinct signatures in B cell chronic lymphocytic leukemias", PNAS, (Aug. 10, 2004), vol. 101, No. 32, pp. 11755-11760.
Bartel, "MicroRNAs: Genomics, Biogenesis, Mechanism, and Function", Cell, (Jan. 23, 2004), vol. 116, pp. 281-297.
Cimmino et al., "miR-15 and miR-16 induce apoptosis by targeting BCL2", PNAS, (Sep. 27, 2005), vol. 102, No. 39, pp. 13944-13949.
Bottoni et al., "miR-15a and miR-16-1 Down-Regulation in Pituitary Adenomas", Journal of Cellular Physiology, (2005), vol. 204, pp. 280-285.
Mosner et al., "Negative feedback regulation of wild-type p53 biosynthesis", The EMBO Journal, (1995), vol. 14, No. 18, pp. 4442-4449.
Esquela-Kerscher et al., "Oncomirs—microRNAs with a role in cancer", Nature Reviews-Cancer, (Apr. 2006), vol. 6, pp. 259-269.
Ju et al., "Regulation of p53 expression by thymidylate synthase", Cell Biology, (Mar. 1999), vol. 96, pp. 2769-3774.
Sinha et al., "Relationships between proto-oncogene expression and apoptosis induced by anticancer drugs in human prostate tumor cells", Biochimica et Biophysica Acta, (1995), vol. 1270, pp. 12-18.
Draghici et al., "Reliability and reproducibility issues in DNA microarray measurements", Trends Genet., (Feb. 2006), vol. 22, No. 2, pp. 101-109.
Bunz et al., "Requirement for p53 and p21 to Sustain G2 Arrest After DNA Damage", Science, (Nov. 20, 1998), vol. 282, pp. 1497-1501.
Ju et al., "Simultaneous gene expression analysis of steady-state and actively translated mRNA populations from osteosarcoma MG-63 cells in response to IL-1a via an open expression analysis platform", Nucleic Acids Research, (2003), vol. 31, No. 17, pp. 5157-5166.
Mattick et al., "Small regulatory RNAs in mammals", Human Molecular Genetics, (2005), vol. 14, Review Issue 1, pp. R121-R132.

(56) References Cited

OTHER PUBLICATIONS

Cummins et al., "The colorectal microRNAome", PNAS, (Mar. 7, 2006), vol. 103, No. 10, pp. 3687-3692.

Fu et al., "Translational regulation of human p53 gene expression", The EMBO Journal, (1996), vol. 15, No. 16, pp. 4392-4401.

Chu et al., "Thymidylate Synthase Protein and p53 mRNA Form an In Vivo Ribonucleoprotein Complex", Molecular and Cellular Biology, (Feb. 1999), vol. 19, No. 2, pp. 1582-1594.

Chu et al., "Identification of a Thymidylate Synthase Ribonucleoprotein Complex in Human Colon Cancer Cells", Molecular and Cellular Biology, (Jan. 1994), vol. 14, No. 1, pp. 207-213.

Sinha et al, "Dissecting microregulation of a master regulatory network", BMC Genomics, (2008), vol. 9:88.

Mishra et al., "A miR-24 microRNA binding-site polymorphism in dihydrofolate reductase gene leads to methotrexate resistance," PNAS, (2007), vol. 104, No. 33, pp. 13513-13518.

Song et al., "miR-192 Regulates Dihydrofolate Reductase and Cellular Proliferation through the p53-microRNA Circuit," Clin. Cancer Res. (2008), vol. 14, pp. 8080-8086.

Negroni et al., "Radioresistance in a tumour cell line correlates with radiation inducible Ku 70/80 end-binding activity," Int. J. Radiat. Biol., (Apr. 2008), vol. 84, No. 4, pp. 265-276.

Braun et al., "p53-Responsive MicroRNAs 192 and 215 Are Capable of Inducing Cell Cycle Arrest," Cancer Res., (2008), vol. 68, pp. 10094-10104.

Georges et al., "Coordinated Regulation of Cell Cycle Transcripts by p53-Inducible microRNAs, miR-192 and miR-215," Cancer Res., (2008), vol. 68, pp. 10105-10112.

Carreras et al., "The Catalytic Mechanism and Structure of Thymidylate Synthase," Annu. Rev. Biochem., (1995), vol. 64, pp. 721-762.

Widemann et al., "Understanding and Managing Methotrexate Nephrotoxicity," The Oncologist, (2006), vol. 11, pp. 694-703.

Drake et al., "Resistance to Tomudex (ZD1694): Multifactorial in Human Breast and Colon Carcinoma Cell Lines," Biochemical Pharmacology, (1996), vol. 51, pp. 1349-1355.

Soong et al., "Prognostic significance of thymidylate synthase, dihydropyrimidine dehydrogenase and tymidine phosphorylase protein expression in colorectal cancer patients treated with or without 5-fluorouracil-based chemotherapy," Ann Oncol., (2008), vol. 19, Issue 5, pp. 915-919.

Yamauchi et al., "Cell-Cycle-Dependant Pharmacology of Methotrexate in HL-60,", J. Pharmacol. Sci., (2005), vol. 99, pp. 335-341.

Xi et al., "Noncoding miRNAs as novel prognostic factor for 5-fluorouracil adjuvant therapy in colorectal cancer," J. of Clinical Oncology, (2006) ASCO Annual Meeting Proceedings (Post-Meeting Edition), vol. 24, No. 185, pp. 1-7.

Volinia et al., "A microRNA expression signature of human solid tumors defines cancer gene targets," PNAS, (2006), vol. 103, No. 7, pp. 2257-2761.

\* cited by examiner

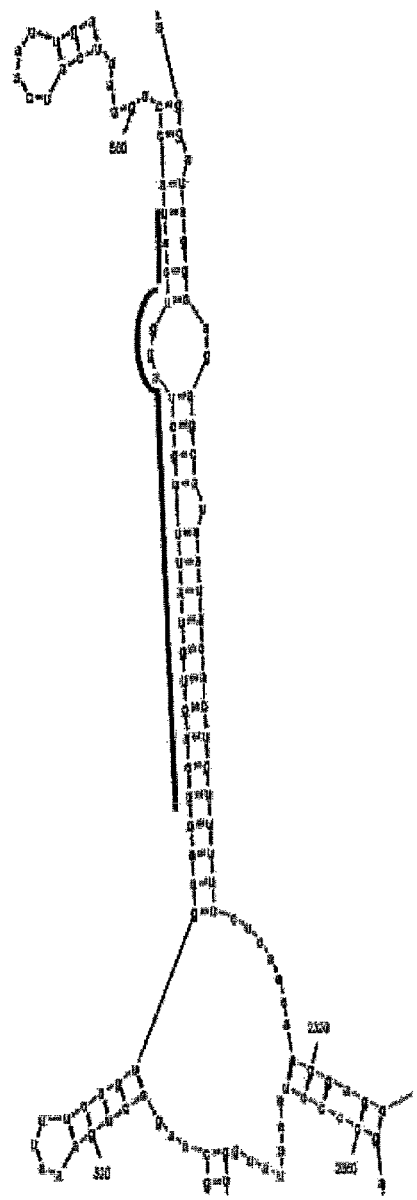
SEQ ID NO. 26  CGACAGUUAAGU-AUCCAGU
SEQ ID NO. 24  GCAGUGUAUUGCUAGGUCA
FIGURE 1A – cont'd.

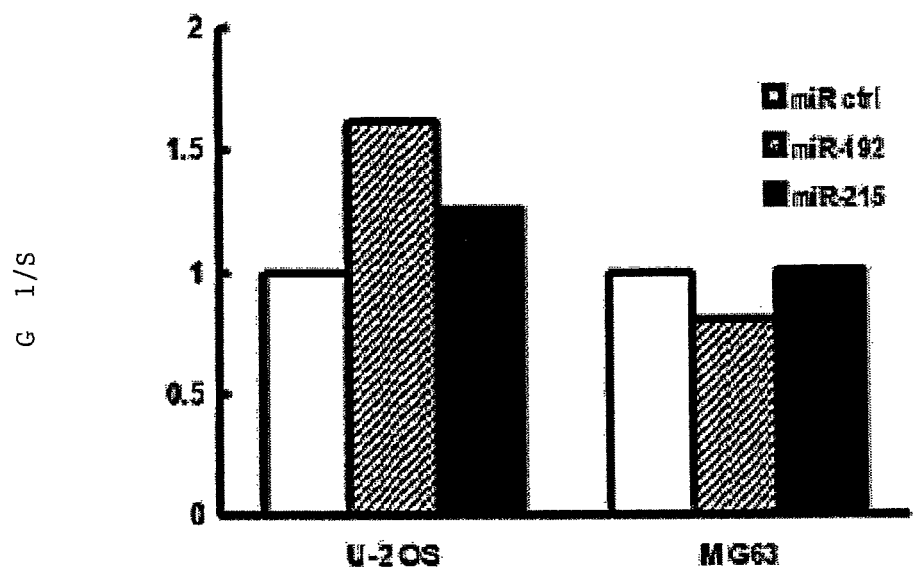
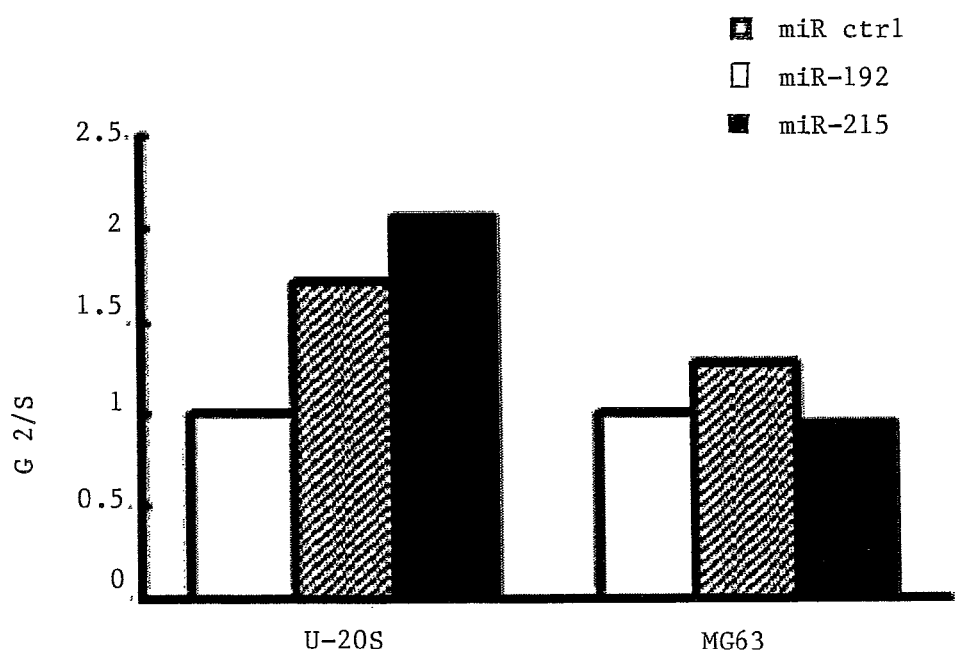
FIGURE 11- cont'd.

A

SEQ ID NO. 27        CAGACAGUUAAGU-AUCCAGUA
                     | ||  |||::  ||||||||
SEQ ID NO. 11        AGCAGTGTATTTGCTAGGTCAT

SEQ ID NO. 28        CCGACAGUUAAGU-AUCCAGUC
                     || ||  |||::  |||||||
SEQ ID NO. 29         GCAGTGTATTTGCTAGGTCAT

B

SEQ ID NO. 27        CAGACAGUUAAGUAUCCAGUA
                                  |||||||
SEQ ID NO. 12        AAGAAAAAGGAACTAGGTCAA

SEQ ID NO. 27        CAGACAGUUAAGUAUCCAGUA
                     ||||  ||||  |  ||||:||
SEQ ID NO. 13        ATCTGACAATGCTGAGGTTAT

SEQ ID NO. 28        CCGACAGUUAAGUAUCCAGUC
                                  |||||||
SEQ ID NO. 12        AAGAAAAAGGAACTAGGTCAA

FIGURE 13

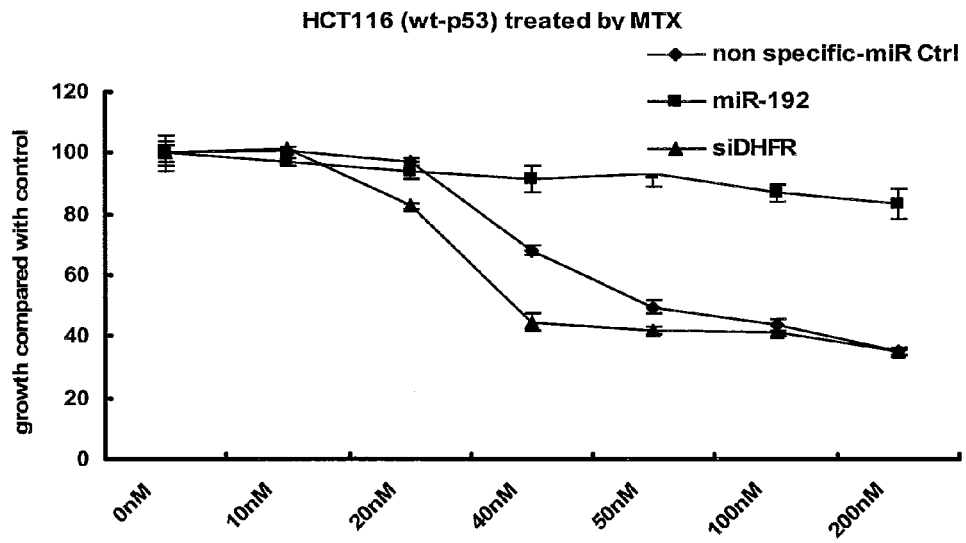
FIGURE 17 A
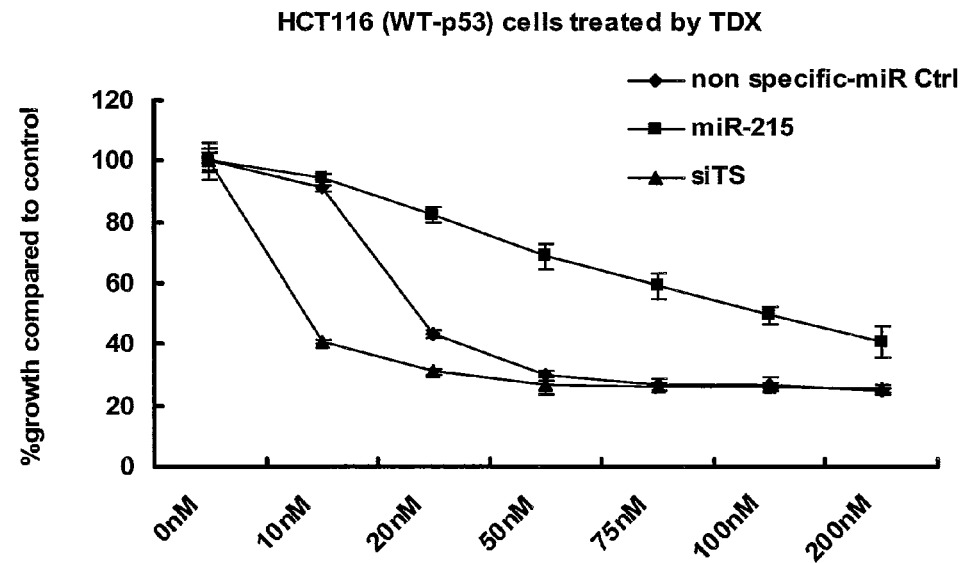

SEQUENCE LISTING

```
<160> NUMBER OF SEQ ID NOS: 29

<210> SEQ ID NO 1
<211> LENGTH: 110
<212> TYPE: RNA
<213> ORGANISM: Artificial Sequence
<220> FEATURE:
<223> OTHER INFORMATION: oligonucleotide

<400> SEQUENCE: 1
gccgagaccg agugcacagg gcucugaccu augaauugac agccagugcu cucgucuccc    60
cucuggcugc caauuccaua ggucacaggu auguucgccu caaugccagc              110

<210> SEQ ID NO 2
<211> LENGTH: 19
```

-continued

<212> TYPE: RNA
<213> ORGANISM: Artificial Sequence
<220> FEATURE:
<223> OTHER INFORMATION: oligonucleotide

<400> SEQUENCE: 2 ugaccauga auugacagc                                                19

<210> SEQ ID NO 3
<211> LENGTH: 21
<212> TYPE: RNA
<213> ORGANISM: Artificial Sequence
<220> FEATURE:
<223> OTHER INFORMATION: oligonucleotide

<400> SEQUENCE: 3 cugaccaug aauugacagc c                                             21

<210> SEQ ID NO 4
<211> LENGTH: 18
<212> TYPE: DNA
<213> ORGANISM: Artificial Sequence
<220> FEATURE:
<223> OTHER INFORMATION: oligonucleotide

<400> SEQUENCE: 4
agcacctccc atgtcacc                                                18

<210> SEQ ID NO 5
<211> LENGTH: 17
<212> TYPE: DNA
<213> ORGANISM: Artificial Sequence
<220> FEATURE:
<223> OTHER INFORMATION: oligonucleotide

<400> SEQUENCE: 5
caaggcagag ccagagc                                                 17

<210> SEQ ID NO 6
<211> LENGTH: 25
<212> TYPE: DNA
<213> ORGANISM: Artificial Sequence
<220> FEATURE:
<223> OTHER INFORMATION: oligonucleotide

<400> SEQUENCE: 6
gctggtggct attttgtcct tgggc                                        25

<210> SEQ ID NO 7
<211> LENGTH: 26
<212> TYPE: DNA
<213> ORGANISM: Artificial Sequence
<220> FEATURE:
<223> OTHER INFORMATION: oligonucleotide

<400> SEQUENCE: 7
cagaatctga ctcccagcac acactc                                       26

<210> SEQ ID NO 8
<211> LENGTH: 59
<212> TYPE: DNA
<213> ORGANISM: Artificial Sequence
<220> FEATURE:
<223> OTHER INFORMATION: oligonucleotide

<400> SEQUENCE: 8
acgcgtccca tgtcaccacc aggggtcgcc atgcctcctg gccttgccca gcaagatct    59

<210> SEQ ID NO 9
<211> LENGTH: 110
<212> TYPE: RNA
<213> ORGANISM: Artificial Sequence
<220> FEATURE:
<223> OTHER INFORMATION: oligonucleotide

<400> SEQUENCE: 9
aucauucaga aaugguauac aggaaaauga ccaugaauu gacagacaau auagcugagu    60
uugucuguca uuucuuuagg ccaauauucu guaugacugu gcuacuucaa             110

<210> SEQ ID NO 10
<211> LENGTH: 21
<212> TYPE: RNA
<213> ORGANISM: Artificial Sequence
<220> FEATURE:
<223> OTHER INFORMATION: oligonucleotide

<400> SEQUENCE: 10
augaccuaug aauugacaga c                                             21

<210> SEQ ID NO 11
<211> LENGTH: 22
<212> TYPE: DNA
<213> ORGANISM: Artificial Sequence
<220> FEATURE:
<223> OTHER INFORMATION: oligonucleotide

<400> SEQUENCE: 11
agcagtgtat ttgctaggtc at                                            22

<210> SEQ ID NO 12
<211> LENGTH: 20
<212> TYPE: DNA
<213> ORGANISM: Artificial Sequence
<220> FEATURE:
<223> OTHER INFORMATION: oligonucleotide

<400> SEQUENCE: 12
aagaaaaaga actaggtcaa                                               20

<210> SEQ ID NO 13
<211> LENGTH: 21
<212> TYPE: DNA
<213> ORGANISM: Artificial Sequence
<220> FEATURE:
<223> OTHER INFORMATION: oligonucleotide

<400> SEQUENCE: 13
atctgacaat gctgaggtta t                                             21

<210> SEQ ID NO 14
<211> LENGTH: 55
<212> TYPE: DNA
<213> ORGANISM: Artificial Sequence
<220> FEATURE:
<223> OTHER INFORMATION: oligonucleotide

<400> SEQUENCE: 14
ctagtagtta actccctgag ggtatctgac aatgctgagg ttatgaacaa agtga        55

<210> SEQ ID NO 15
<211> LENGTH: 55

```
<212> TYPE: DNA
<213> ORGANISM: Artificial Sequence
<220> FEATURE:
<223> OTHER INFORMATION: oligonucleotide

<400> SEQUENCE: 15
agcttcactt tgttcataac ctcagcattg tcagataccc tcagggagtt aacta        55

<210> SEQ ID NO 16
<211> LENGTH: 55
<212> TYPE: DNA
<213> ORGANISM: Artificial Sequence
<220> FEATURE:
<223> OTHER INFORMATION: oligonucleotide

<400> SEQUENCE: 16
ctagtagtta actccctgag ggtatatcac gatgttgata tcacgaacaa agtga        55

<210> SEQ ID NO 17
<211> LENGTH: 55
<212> TYPE: DNA
<213> ORGANISM: Artificial Sequence
<220> FEATURE:
<223> OTHER INFORMATION: oligonucleotide

<400> SEQUENCE: 17
agcttcactt tgttcgtgat atcaacatcg tgatataccc tcagggagtt aacta        55

<210> SEQ ID NO 18
<211> LENGTH: 55
<212> TYPE: DNA
<213> ORGANISM: Artificial Sequence
<220> FEATURE:
<223> OTHER INFORMATION: oligonucleotide

<400> SEQUENCE: 18
ctagtagttc tttttgctct aaaagaaaaa ggaactaggt caaaaatctg tccga        55

<210> SEQ ID NO 19
<211> LENGTH: 55
<212> TYPE: DNA
<213> ORGANISM: Artificial Sequence
<220> FEATURE:
<223> OTHER INFORMATION: oligonucleotide

<400> SEQUENCE: 19
agcttcggac agattttga cctagttcct ttttctttta gagcaaaaag aacta         55

<210> SEQ ID NO 20
<211> LENGTH: 66
<212> TYPE: DNA
<213> ORGANISM: Artificial Sequence
<220> FEATURE:
<223> OTHER INFORMATION: oligonucleotide

<400> SEQUENCE: 20
ctagtaattt cagtgaaagc agtgtatttg ctaggtcata ccagaaatca tcaattgagg   60
tacgga                                                             66

<210> SEQ ID NO 21
<211> LENGTH: 66
<212> TYPE: DNA
<213> ORGANISM: Artificial Sequence
<220> FEATURE:
<223> OTHER INFORMATION: oligonucleotide
```

```
<400> SEQUENCE: 21
agcttccgta cctcaattga tgatttctgg tatgacctag caaatacact gctttcactg    60
aaatta                                                               66

<210> SEQ ID NO 22
<211> LENGTH: 66
<212> TYPE: DNA
<213> ORGANISM: Artificial Sequence
<220> FEATURE:
<223> OTHER INFORMATION: oligonucleotide

<400> SEQUENCE: 22
ctagtaattt cagtgaaagc agtgtgcttg cgatatgata ccagaaatca tcaattgagg    60
tacgga                                                               66

<210> SEQ ID NO 23
<211> LENGTH: 66
<212> TYPE: DNA
<213> ORGANISM: Artificial Sequence
<220> FEATURE:
<223> OTHER INFORMATION: oligonucleotide

<400> SEQUENCE: 23
agcttccgta cctcaattga tgatttctgg tatcatatcg caagcacact gctttcactg    60
aaatta                                                               66

<210> SEQ ID NO 24
<211> LENGTH: 20
<212> TYPE: RNA
<213> ORGANISM: Artificial Sequence
<220> FEATURE:
<223> OTHER INFORMATION: oligonucleotide

<400> SEQUENCE: 24
gcaguguauu ugcuagguca                                                20

<210> SEQ ID NO 25
<211> LENGTH: 23
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (11)..(13)
<223> OTHER INFORMATION: internucleotide linkages, e.g.
      phosphorothioates for nuclease resistance

<400> SEQUENCE: 25
cgccatgcct nnnggccttg ccc                                            23

<210> SEQ ID NO 26
<211> LENGTH: 19
<212> TYPE: RNA
<213> ORGANISM: Artificial Sequence
<220> FEATURE:
<223> OTHER INFORMATION: oligonucleotide

<400> SEQUENCE: 26
cgacaguuaa guauccagu                                                 19

<210> SEQ ID NO 27
<211> LENGTH: 21
<212> TYPE: RNA
```

```
<213> ORGANISM: Artificial Sequence
<220> FEATURE:
<223> OTHER INFORMATION: oligonucleotide

<400> SEQUENCE: 27
cagacaguua aguauccagu a                                              21

<210> SEQ ID NO 28
<211> LENGTH: 21
<212> TYPE: RNA
<213> ORGANISM: Artificial Sequence
<220> FEATURE:
<223> OTHER INFORMATION: oligonucleotide

<400> SEQUENCE: 28
ccgacaguua aguauccagu c                                              21

<210> SEQ ID NO 29
<211> LENGTH: 21
<212> TYPE: DNA
<213> ORGANISM: Artificial Sequence
<220> FEATURE:
<223> OTHER INFORMATION: oligonucleotide

<400> SEQUENCE: 29
gcagtgtatt tgctaggtca t                                              21
```

MIRNAS AS THERAPEUTIC TARGETS IN CANCER

STATEMENT REGARDING FEDERALLY SPONSORED RESEARCH AND DEVELOPMENT

The invention was made using U.S. Government funds, and therefore the U.S. Government has rights in the invention.

FIELD OF THE INVENTION

The present invention relates to compositions and methods relating to the identification and characterization of genes and biological pathways related to these genes as represented by the expression of the identified genes, as well as use of microRNAs (miRNAs) related to such, for therapeutic, prognostic, and diagnostic applications, particularly those methods and compositions related to assessing and/or identifying pathological conditions directly or indirectly related to miR-192 or miR-215.

BACKGROUND OF THE INVENTION

Dihydrofolate reductase (DHFR) and Thymidylate Synthase (TS) are two key enzymes for DNA synthesis and represent some of the most important targets for cancer chemotherapy. DHFR catalyzes the reduction of folate and 7, 8 dihydrofolate to 5, 6, 7, 8 tetrahydrofolate, the latter as the one-carbon donor is essential for the formation of thymidylate (dTMP) which is the precursor for DNA synthesis (see Banerjee et al., "Novel aspects of resistance to drugs targeted to dihydrofolate reductase and thymidylate synthase, Biochim. Biophys. Acta. (2002) 1587: 164-173). TS catalyzes the reductive methylation of dUMP by CH2H4folate to produce dTMP and H2folate (see Carreras et al., "The catalytic mechanism and structure of thymidylate synthase," Annu. Rev. Biochem. (1995) 64: 721-762). DHFR inhibitors, such as methotrexate (MTX), and TS inhibitors, such as 5-fluorouracil (5-FU) and Tomudex or Ralitrexed (TDX, ZD1694), are widely used chemotherapeutic drugs for the treatment of osteosarcoma and colon cancer (see Widemann et al., "Understanding and managing methotrexate nephrotoxicity," Oncologist. (2006) 11: 694-703; see also Calvert, "An overview of folate metabolism: features relevant to the action and toxicities of antifolate anticancer agents," Semin. Oncol. (1999) 26: 3-10).

As such, TS and DHFR are the major targets of cancer chemotherapy in the clinic today. TDX, the third-generation TS inhibitor, is an active agent in the treatment of human colon and breast cancer (see Drake et al., "Resistance to tomudex (ZD1694): multifactorial in human breast and colon carcinoma cell lines," Biochem. Pharmacol. (1996) 51: 1349-1355). The inhibitor of DHFR, such as MTX, is widely used in the treatment of human leukemia, osteosarcoma and choriocarcinoma. Increased DHFR protein levels are reported to be associated with drug resistance (see Banerjee et al., "Novel aspects of resistance to drugs targeted to dihydrofolate reductase and thymidylate synthase," Biochem. Biophys. Acta. (2002) 1587: 164-173), and low tumor expression levels of TS have also been linked with improved outcome for colon cancer patients treated with 5-FU chemotherapy (see Soong et al., "Prognostic significance of thymidylate synthase, dihydropyrimidine dehydrogenase and thymidine phosphorylase protein expression in colorectal cancer patients treated with or without 5-fluorouracil-based chemotherapy," Ann. Oncol. (2008) 19: 915-919). However, MTX has the highest activity at the time when DNA synthesis, DHFR activity, DHFR content, and DHFR mRNA content increased and the lowest activity at the time when they decreased (see Yamauchi et al., "Ohdo S. Cell-cycle-dependent pharmacology of methotrexate in HL-60," J. Pharmacol. Sci. (2005) 99: 335-341).

Thus, there exists a need for better prognostic and diagnostic measures, treatment and control of neoplasm through application of small molecules to target cells to affect various cellular components, such as TS and DHFR involved in cellular proliferation of neoplasia.

SUMMARY OF THE INVENTION

The invention provides an isolated inhibitory nucleic acid molecule that is complementary to at least a portion of miR-192 (SEQ ID NO:1) or miR-215 (SEQ ID NO:9). The inhibitory nucleic acid molecule decreases the expression of the at least a portion of miR-192 or miR-215 in a cell. In an embodiment, the nucleic acid molecule is an antisense nucleic acid molecule. The antisense nucleic acid molecule has at least an 85% sequence identity to the portion of miR-192 (SEQ ID NO:1), miR-215 (SEQ ID NO:9). In another embodiment, the portion has a sequence selected from the group consisting of SEQ ID NOs:2, 3 and 10. In this embodiment, the inhibiting nucleic acid molecule has at least 85% sequence identity to the sequence. In another embodiment, the nucleic acid molecule has a sequence consisting essentially of SEQ ID NOs: 1-3 or 9-10. In another embodiment, an expression vector comprises the inhibitory nucleic acid molecule. The inhibitory nucleic acid molecule may be operably linked to a promoter suitable for expression in a mammalian cell. The vector may be a viral vector. In another embodiment, a cell comprises the vector.

The invention further provides an isolated inhibitory nucleic acid molecule that corresponds to at least a portion of miR-192 (SEQ ID NO:1) or miR-215 (SEQ ID NO:9). The inhibitory nucleic acid molecule decreases the expression of the miR-192 (SEQ ID NO:1) or miR-215 (SEQ ID NO:9) in a cell. In one embodiment, the portion has a sequence selected from the group consisting of SEQ ID NOs:2, 3 and 10. In another embodiment, the nucleic acid molecule has a sequence consisting essentially of SEQ ID NOs:1-3 or 9-10. In another embodiment, the inhibiting nucleic acid molecule has at least 85% sequence identity to the portion of SEQ ID NOs: 1 or 9, or at least 85% sequence identity to SEQ ID NOs:2, 3 or 10. The nucleic acid molecule is also an shRNA or an siRNA. In an embodiment, the nucleic acid molecule comprises at least one modification. The modification may be a non-natural internucleotide linkage, a backbone modification, or a substituted sugar moiety. In another embodiment, an expression vector comprises the inhibitory nucleic acid molecule. The inhibitory nucleic acid molecule may be operably linked to a promoter suitable for expression in a mammalian cell. The vector may be a viral vector. In another embodiment, a cell comprises the vector.

The invention further provides an isolated inhibitory nucleic acid molecule that corresponds to a portion of a miR-192 promoter that binds to a p53 binding sequence (SEQ ID NO: 25). The inhibitory nucleic acid molecule comprises or consists essentially of a sequence or a complementary sequence of SEQ ID NO:25, a fragment thereof, or a variant thereof. In this embodiment, the inhibitory nucleic acid molecule has at least 85% sequence identity to SEQ ID NO: 25 or a fragment thereof.

Methods for delivery of the inhibitory nucleic acid molecules include, but are not limited to, using a delivery system such as viral vectors, liposomes, polymers, microspheres, gene therapy vectors, naked DNA vectors, carbon nanotubes and chemical linkers. One of ordinary skill in the art would recognize other methods of delivering the inhibitory nucleic acid molecules into the cell or subject.

The invention further provides a method of modulating expression of a component of a cell, comprising contacting the cell with a nucleic acid comprising a portion of a sequence or a complementary sequence selected from an miR-192 sequence (SEQ ID NO:1), an miR-215 nucleic acid sequence (SEQ ID NO:9), miR-192 promoter binding site for p53 (SEQ ID NO:25), an antisense miR-192 sequence, an antisense miR-215 sequence and an antisense to the miR-192 promoter binding site for p53 in an amount sufficient to modulate the cellular component. In an embodiment, the nucleic acid is an antisense nucleic acid. The nucleic acid may be an siRNA or an shRNA. In an embodiment, the cellular component is miR-192 or miR-215. In another embodiment, the portion has a sequence selected from the group consisting of SEQ ID NOs:2, 3, 10, antisense SEQ ID NO: 2 and antisense SEQ ID NO: 3 and an antisense SEQ ID NO: 10. In another embodiment, the nucleic acid molecule has a sequence consisting essentially of SEQ ID NOs:1-3, 9-10, 25 or antisense sequences thereof. In another embodiment, the cellular component is p21 or p53. In another embodiment, the cellular component is regulated by p53. In another embodiment, the cellular component is DHFR or TS.

The invention further provides a method of modulating proliferation of a cell, comprising contacting the cell with a nucleic acid having a sequence or a complementary sequence to at least a portion of miR-192 (SEQ ID NO:1), miR-215 (SEQ ID NO:9), a p53 region that binds to a miR-192 promoter or the miR-192 promoter that binds to p53 (SEQ ID NO:25) in an amount effective to modulate proliferation of the cell. In another embodiment, the nucleic acid is an antisense nucleic acid. In another embodiment, the portion has a sequence selected from the group consisting of SEQ ID NOs: 2, 3, 10 and 25. In another embodiment, the nucleic acid molecule has a sequence consisting essentially of SEQ ID NOs:1-3, 9-10 or 25 or an antisense sequence thereof. In another embodiment, the nucleic acid is an siRNA or an shRNA. In another embodiment, the cell is a cancer stem cell. In another embodiment, the cell is a neoplastic cell. In another embodiment, the method of modulating proliferation of a cell is a method of increasing the proliferation of a cell.

The invention further provides a method of increasing the sensitivity of a cell to a chemotherapeutic agent, comprising contacting the cell with a nucleic acid complementary to at least a portion of miR-192 (SEQ ID NO:1), miR-215 (SEQ ID NO:9) an miR-192 promoter binding site for p53 (SEQ ID NO:25) or a p53 region that binds to the miRNA-192 promoter, in an amount effective to sensitize the cell to the chemotherapeutic agent. Examples of chemotherapeutic agents include, but are not limited to, methotrexate, fluorouracil (5-FU), nolatrexed, ZD9331, GS7904L and ralitrexed. In another embodiment, the portion has a sequence selected from the group consisting of SEQ ID NOs:2, 3, 10 and 25. In another embodiment, the nucleic acid molecule has a sequence consisting essentially of SEQ ID NOs:1-3, 9-10, and 25. In embodiments, the nucleic acid is an antisense nucleic acid. In another embodiment, the nucleic acid is an siRNA or an shRNA. In another embodiment, the cell is a cancer stem cell. In another embodiment, the cell is a neoplastic cell.

The invention further provides a method of increasing the sensitivity of a cell to radiation, comprising contacting the cell with a nucleic acid complementary to at least a portion of miR-192 (SEQ ID NO:1), miR-215 (SEQ ID NO:9) an miR-192 promoter binding site for p53 (SEQ ID NO:25) or a p53 region that binds to the miRNA-192 promoter, in an amount effective to sensitize the cell to radiation. In embodiments, the nucleic acid is an antisense nucleic acid. In another embodiment, the nucleic acid is an siRNA or an shRNA. In another embodiment, the portion has a sequence selected from the group consisting of SEQ ID NOs:2, 3 and 10. In another embodiment, the nucleic acid molecule has a sequence consisting essentially of SEQ ID NOs:1-3, 9-10, and 25. In another embodiment, the cell is a cancer stem cell. In another embodiment, the cell is a neoplastic cell.

The invention further provides a method of treating a neoplasm in a subject, comprising administering to the subject an effective amount of a nucleic acid molecule that inhibits expression of miR-192 or miR-215, and a second therapy, wherein inhibition of expression of miR-192 or miR-215 sensitizes the neoplasm to the second therapy. In another embodiment, the second therapy comprises administering a chemotherapeutic agent. In one embodiment, the chemotherapeutic agent is selected from the group consisting of a DHFA inhibitor and examples of chemotherapeutic agents include, but are not limited to, methotrexate, fluorouracil (5-FU), nolatrexed, ZD9331, GS7904L and ralitrexed. In another embodiment, the second therapy comprises administering radiation to the subject. The neoplasm may be cancer. The cancer may be selected from the group consisting of colon cancer, pancreatic cancer, lung cancer, breast cancer, cervical cancer, gastric cancer, kidney cancer, leukemia, liver cancer, lymphoma, ovarian cancer, prostate cancer, rectal cancer, sarcoma, skin cancer, testicular cancer, and uterine cancer.

The invention further provides a method of diagnosing a neoplasm in a subject comprising determining the level of expression of miR-192 or miR-215. In one embodiment, the method of diagnosing the neoplasm in the subject comprises determining the level of expression of miR-192 and miR-215.

The invention further provides a method of identifying a neoplasm resistant to chemotherapy comprising determining the level of expression in the neoplasm of miR-192 or miR-215, and identifying the neoplasm as resistant to therapy if the level of the miR-215 is elevated or the level of miR-192 is reduced as compared to a control. In one embodiment the method of identifying the neoplasm resistant to chemotherapy comprises determining the levels of miR-192 and miR-215, and identifying the neoplasm as resistant to therapy if the levels of miR-192 and miR-215 are elevated.

The invention further provides a method of determining whether a neoplasm is a candidate for treatment with a chemotherapeutic agent comprising evaluating the level of expression of an miRNA, wherein the miRNA is miR-192 or miR-215, and rejecting the candidate if the expression of the miRNA is elevated; or accepting the candidate if the expression of the miRNA is reduced. In one embodiment, the miRNA is miR-192 and miR-215. In another embodiment, the rejected candidate would be a candidate for the methods of increasing sensitivity or treating a neoplasm discussed herein.

The invention further provides a kit for analysis of a pathological sample. The kit comprising in a suitable container an miRNA hybridization reagent for determining the level of miR-192 or miR-215. In an embodiment, the mRNA hybridization reagent comprises a hybridization probe. In another embodiment, the mRNA hybridization reagent comprises amplification primers. In another embodiment, the hybridization probe or amplification primers complementary to a sequence selected from the group consisting of SEQ ID NOs: 1, 2, 3, 9, 10 and fragments thereof. The pathological sample can be any sample commonly taken from a subject, such as, for example, blood, urine, tissue, or other bodily fluid.

The invention further provides a method of identifying an agent that inhibits expression of an miRNA selected from the group consisting of miR-192 and miR-215, which comprises contacting a cell that expresses the miRNA with an agent, and comparing the expression level of the miRNA in the cell contacted by the agent with the expression level of the miRNA in the absence of the agent, wherein the agent is an inhibitor of the miRNA if expression of the miRNA is reduced. In an embodiment, the test cell overexpresses the miRNA.

BRIEF DESCRIPTION OF THE FIGURES

FIG. 13 provides alignments of miR-215 with regions of DHFR and TS.

FIG. 17 shows that the effect of miR-192 (Panel A) or miR-215 (Panel B) on proliferation of HCT-116 (wt-p53) cells treated with methotrexate.

DETAILED DESCRIPTION OF THE INVENTION

Figure 11:
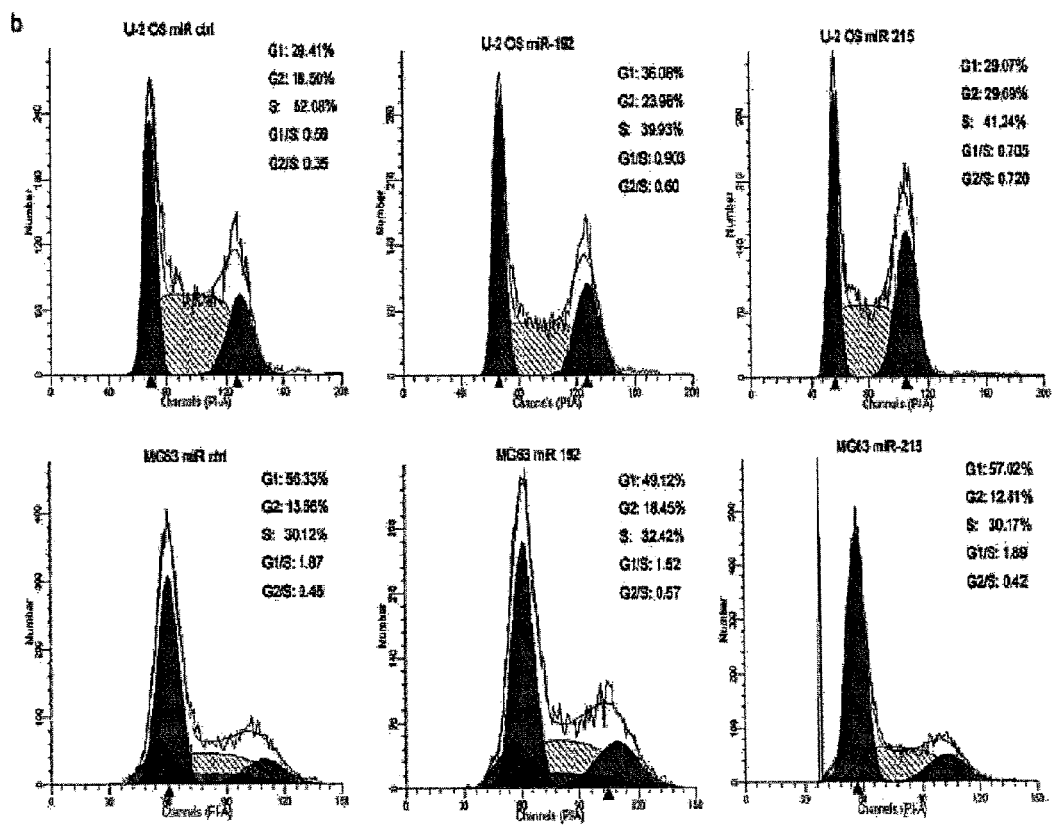
FIG. 11 depicts proportions of cultured U-2 OS or MG63 cells, and U-2 OS or MG63 cells transfected with miR-192 or miR-215 at various stages of the cell cycle.

The inventors have discovered that miR-192 and miR-215, individually, decrease the expression of TS and DHFR protein, and further found that miR-192 and miR-215, individually, change the sensitivity of cancerous cells such as, for example, HCT-116 (wt-p53) or U-2 OS cells to TDX or MTX. The inventors have found that down-regulation of TS or DHFR protein by a siRNA specific against TS or DHFR increases the sensitivity of TDX or MTX in the colon cancer or osteosarcoma cell lines, whereas even though miR-192 and miR-215 also down-regulated the expression levels of TS or DHFR, they did not increase the chemosensitivity of TDX or MTX compared to a non-specific miRNA control. TDX or MTX are considered to be more effective on the cells in the S-phase. As illustrated in FIGS. 5 and 11, siRNAs specific against TS or DHFR do not decrease the cells in the S-phase, whereas the cells in the S-phase were reduced in the miR-192 transfected cells and miR-215 transfected cells. Thus, down-regulating miR-192 or miR-215 increases the sensitivity of a cell or a subject to chemotherapy.

The inventors have found that colon cancer stem cells depend on, at least in part, elevated miR-192 or miR-215 to have a reduced cell proliferation phenotype. The advantage of tumor stem cells using miR-192 or miR-215 to achieve this is that translational control by miR-192 or miR-215 is an acute response, readily reversible without permanently degrading its target mRNAs such as TS and DHFR or trigger apoptosis. This also suggests why half of the colon cancer cases containing wild type p53 are still resistant to chemotherapeutic treatment. This mechanism also provides a novel approach to selectively killing colon cancer stem cells by inhibiting miR-192 or miR-215 and subsequently eliminating them with chemotherapeutic agents. Furthermore, this mechanism also provides a novel approach for identifying a candidate who will respond to chemotherapeutic treatment by inhibiting miR-192 and/or miR-215.

In certain aspects, the invention is directed to methods for the assessment, analysis, and/or therapy of a cell or subject where certain genes have a reduced or increased expression (relative to normal) as a result of an increased or decreased expression of miR-192 or miR-215. The expression profile and/or response to miR-192 or miR-215 expression or inhibition may be indicative of a disease or an individual with a pathological condition such as, for example, cancer.

According to a first embodiment, the miR-192 or miR-215 inhibitors may include antisense nucleic acids or molecules. Antisense nucleic acids are effective in inhibiting human miRNAs. Antisense nucleic acids include non-enzymatic nucleic acid compounds that bind to a target nucleic acid by, for example, RNA-RNA, RNA-DNA or RNA-PNA interactions and effect the target nucleic acid. Generally, these molecules are complementary to a target sequence along a single contiguous sequence of the antisense nucleic acid. In this embodiment, the antisense nucleic acid reduces expression of miR-192 or miR-215.

In another embodiment, the inhibitors include fragments of the nucleic acid molecules that bind to miR-192 (SEQ ID NO:1) or miR-215 (SEQ ID NO:9), bind to an miR-192 promoter binding sequence for p53 (SEQ ID NO:25), or bind to the p53 sequence that is complementary to the miR-192 promoter. A suitable fragment can be at least 8, at least 10, at least 12, at least 14, at least 16, at least 18, at least 19, at least 20, at least 21, at least 22, at least 23, at least 24, or at least 25 nucleotides in length. Non-limiting examples of suitable fragments include nucleic acids having sequences complementary to SEQ ID NOs:2, 3, 9 or fragments thereof. One of ordinary skill in the art recognizes that nucleic acids complimentary to other portions of SEQ ID NO:1 or SEQ ID NO:9 would be equally effective.

In another embodiment, antisense nucleic acids may also bind to a substrate nucleic acid and form a loop. In this embodiment, the antisense nucleic acids may be complementary to two or more non-contiguous substrate sequences and/or two or more non-contiguous sequence portions of an antisense nucleic acid may be complementary to a target sequence.

In another embodiment, antisense nucleic acids may be complementary to a guide strand of an miRNA positioned in the RNA silencing complex. In another embodiment, antisense nucleic acids may be used to target a nucleic acid by means of DNA-RNA interactions. In this embodiment, RNase H is activated to digest the target nucleic acid as would be understood by one of ordinary skill in the art. For example, the antisense nucleic acids may comprise one or more RNase H activating region capable of activating RNase H to cleave a target nucleic acid. The RNase H activating region may comprise any suitable backbone. For example, in this embodiment, the RNase H activating region may comprise a phosphodiester, phosphorothioate, phosphorodithioate, 5'-thiophosphate, phosphoramidate and/or methylphosphonate.

In another embodiment, the nucleic acid molecule may comprise one or more modifications. Antisense nucleic acids according to the embodiments may comprise natural-type oligonucleotides and modified oligonucleotides. For example, in this embodiment, the antisense nucleic acid may comprise phosphorothioate-type oligodeoxyribonucleotides, phosphorodithioate-type oligodeoxyribonucleotides, methylphosphonate-type oligodeoxyribonucleotides, phosphoramidate-type oligodeoxyribonucleotides, H-phosphonate-type oligodeoxyribonucleotides, triester-type oligodeoxyribonucleotides, alpha-anomer-type oligodeoxyribonucleotides, peptide nucleic acids, locked nucleic acids, and nucleic acid-modified compounds. It will be readily apparent to one of ordinary skill in the art that other oligonucleotides are within the scope and spirit of this invention.

In another embodiment, the modification may comprise internucleoside linkages. For example, an inhibitory nucleic acid may be based on 2'-modified oligonucleotides containing oligodeoxynucleotide gaps with internucleotide linkages modified to phosphorothioates for nuclease resistance. The presence of methylphosphonate modifications increases the affinity of the oligonucleotide for its target RNA and thus increases its effectiveness in inhibiting the target RNA. This modification also increases the nuclease resistance of the modified oligonucleotide.

In another embodiment, the modification may comprise a backbone modification. For example, oligomers having modified backbones may include those that retain a phosphorus atom in the backbone and those that do not have a phosphorus atom in the backbone. For example, nucleobase oligomers that have modified oligonucleotide backbones include, but are not limited to, phosphorothioates, chiral phosphorothioates, phosphorodithioates, phosphotriesters, aminoalkyl-phosphotriesters, methyl and other alkyl phosphonates, phosphinates, phosphoramidates, thionophosphoramidates, thionoalkylphosphonates, thionoalkylphosphotriesters, and boranophosphates. Other forms, including, but not limited to, salts, mixed salts and free acid forms, are also contemplated.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include, but are not limited to, those having morpholino linkages, siloxane backbones, sulfide, sulfoxide and sulfone backbones, formacetyl and thioformacetyl backbones, methylene formacetyl and thioformacetyl backbones, alkene containing backbones, sulfamate backbones, methyleneimino and methylenehydrazino backbones, sulfonate and sulfonamide backbones, and/or amide backbones.

In another embodiment, the modification may also comprise one or more substituted sugar moieties. For example, the RNase H activating region may comprise deoxyribose, arabin and/or fluoroarabino nucleotide sugar chemistry. Such modifications may also include 2'-O-methyl and 2'-methoxyethoxy modifications, 2'-dimethylaminooxyethoxy, 2'-aminopropoxy and 2'-fluoro, and modifications at other positions on the oligonucleotide or other nucleobase oligomer, particularly the 3' position of the sugar on the 3' terminal nucleotide. Nucleobase oligomers may also have sugar mimetics. In another embodiment, both the sugar and the internucleoside linkage may be replaced with novel groups. The nucleobase units are maintained for hybridization with at least a portion of miR-192 (SEQ ID NO:1), miR-215 (SEQ ID NO:9), an miR-192 promoter sequence that binds to p53 (SEQ ID NO:25) or the p53 sequence that binds to the miR-192 promoter (SEQ ID NO:25).

Those skilled in the art will recognize that the foregoing are non-limiting examples and that any combination of phosphate, sugar and base chemistry of a nucleic acid that supports the activity of RNase H enzyme is within the scope of the present invention.

According to another embodiment, the invention relates to the use of interference RNA (RNAi) to alter the expression of miR-192 or miR-215. In one embodiment, the expression is altered by reducing the expression of miR-192 or miR-215. In another embodiment, the expression of miR-192 and miR- 215 is altered. In another embodiment, the expression is altered by reducing the expression of miR-192 and miR-215, RNAi comprises double stranded RNA that can specifically block expression of a target gene. Double-stranded RNA (dsRNA) blocks gene expression in a specific and post-transcriptional manner. RNAi provides a useful method of inhibiting gene expression in vitro or in vivo. RNAi can comprise either long stretches of dsRNA identical or substantially identical to the target nucleic acid sequence or short stretches of dsRNA identical to or substantially identical to only a region of the target nucleic acid sequence.

In embodiments RNAi includes, but are not limited to, small interfering RNAs (siRNAs), small hairpin RNAs (shRNAs), and other RNA species, such as non-enzymatic nucleic acids, which can be cleaved in vivo to form siRNAs. In this embodiment, RNAi may also include RNAi expression vectors capable of giving rise to transcripts which form dsRNAs or shRNAs in cells, and/or transcripts which can produce siRNAs in vivo.

The RNAi may comprise a nucleotide sequence that hybridizes under physiologic conditions of the cell to the nucleotide sequence of at least a portion of the RNA transcript for the target gene. These RNAi have the advantage of being able to tolerate variations in sequence that may arise from, for example, genetic mutation, strain polymorphism or evolutionary divergence. The number of tolerated nucleotide mismatches between the target sequence and the RNAi sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition. In this embodiment, the antisense nucleic acid molecule has at least 85% sequence identity to SEQ ID NOs: 1-3, 9 or 10.

Sequence identity may be optimized by sequence comparison and alignment algorithms known in the art and calculating the percent difference between the nucleotide sequences. In this embodiment, the preferred sequence identity between the inhibitory RNA and the portion of the target gene is greater than 90%, 95%, 96%, 97%, 98%, 99% or 100%. Alternatively, the duplex region of the RNA may be defined functionally as a nucleotide sequence that is capable of hybridizing under specified conditions with a portion of the target gene transcript.

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses of double-stranded material may yield more effective inhibition, while lower doses may also be useful for specific applications. Inhibition is sequence-specific in that nucleotide sequences corresponding to the duplex region of the RNA are targeted for genetic inhibition.

In this embodiment, the siRNAs are around 19-30 nucleotides long, and even more preferably 21-23 nucleotides. The siRNAs effectively recruit nuclease complexes and guide the complexes to the target mRNA by pairing to the specific sequences. As a result, the target mRNA is degraded by the nucleases in the protein complex. In embodiments, the 21-23 nucleotides siRNA molecules comprise a 3' hydroxyl group. In certain embodiments, the siRNA can be generated by the processing of longer double-stranded RNAs, for example, in the presence of the enzyme dicer. The siRNA molecules can be purified using a number of techniques known to those of skill in the art such as, for example, gel electrophoresis, non-denaturing column chromatography, chromatography, glycerol gradient centrifugation, and/or affinity purification with an antibody.

In this embodiment, the shRNAs can be synthesized exogenously or can be formed by transcribing from RNA polymerase III promoters in vivo. Examples of making and using such shRNAs for gene silencing in mammalian cells are known in the art. Preferably, such shRNAs are engineered in cells or in an animal to ensure continuous and stable suppression of a desired gene. It is recognized in the art that siRNAs can be produced by processing a shRNA in the cell.

In another embodiment, the invention relates to the use of suitable ribozyme molecules, such as, for example, RNA endoribonucleases and hammerhead ribozymes, designed to catalytically cleave mRNA transcripts to prevent translation of mRNA. Hammerhead ribozymes cleave mRNAs at locations dictated by flanking regions that form complementary base pairs with the target mRNA, which have a base sequence of 5'-UG-3'.

According to another embodiment, polynucleotide or expression vector therapy for treating neoplasia featuring a polynucleotide encoding an inhibitory nucleic acid molecule or analog thereof that targets miR-192 or miR-215 is provided. In this embodiment, the antisense nucleic acid may cause inhibition of expression by hybridizing with miR-192 or miR-215 and/or genomic sequences encoding miR-192 or miR-215. Expression vectors encoding inhibitory nucleic acid molecules can be delivered to cells of a subject having a neoplasia in a form in which they can be taken up and expressed so that therapeutically effective levels may be achieved. The expression vector produces an oligonucleotide which is complementary to at least a unique portion of miR-192 or miR-215. Methods for delivery of the polynucleotides to the cell according to the invention include, but are not limited to, using a delivery system such as viral vectors, liposomes, polymers, microspheres, gene therapy vectors, naked DNA vectors, carbon nanotubes and chemical linkers. One of ordinary skill in the art would recognize other methods of delivering polynucleotides into the cell or subject. Nucleic acid probes may also be modified so that they are resistant to endogenous nucleases such as, for example, exonucleases and/or endonucleases, and are therefore stable in vivo.

Inhibitory nucleic acid molecule expression for use in polynucleotide therapy methods can be directed from any suitable promoter and regulated by any appropriate mammalian regulatory element. Promoters may include, but are not limited to, the human cytomegalovirus, simian virus 40, and/or metallothionein promoters. In this embodiment, enhancers known to preferentially direct gene expression in specific cell types can be used to direct the expression of a nucleic acid. The enhancers used can include, without limitation, those that are characterized as tissue- or cell-specific enhancers.

Transducing viral vectors such as, for example, retroviral, adenoviral, lentiviral and adeno-associated viral vectors, can be used as expression vectors for somatic cell gene therapy. Viral vectors are especially useful because of their high efficiency of infection, and stable integration and expression. In this embodiment, for example, a polynucleotide encoding an inhibitory nucleic acid molecule can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus.

In another embodiment, the invention comprises an inhibitory nucleic acid molecule that corresponds to a portion of a miR-192 promoter binding sequence for p53 (SEQ ID NO:25). The inhibitory nucleic acid molecule comprises or consists essentially of a sequence or a complementary sequence of SEQ ID NO:25, a fragment thereof or a variation thereof. The inventors have discovered that SEQ ID NO:25 is a portion of the miR-192 promoter (SEQ ID NO:8) that binds to p53. Accordingly, the expression of miR-192 can be altered by administering an inhibitory nucleic acid molecule that comprises a sequence of SEQ ID NO:25, a fragment thereof, or a variation thereof. In this embodiment, the inhibitory nucleic acid molecule would bind to the p53 site at the miR-192 promoter binding site and thereby block the binding of p53 to the miR-192 promoter. The expression of miR-192 can also be altered by administering an inhibitory nucleic acid molecule that comprises a sequence complementary to SEQ ID NO:25, a fragment thereof, or a variation thereof. In this embodiment, the inhibitory nucleic acid molecule would bind to the miR-192 promoter thereby blocking p53 from binding to the miR-192 promoter region and block transcription of miR-192.

The inhibitory nucleic acid molecule can consist essentially of a sequence or a sequence complementary to SEQ ID NO:25, a fragment thereof, or a variation. In such embodiments, the inhibitory nucleic acid molecule may contain other components that are not involved in binding to the p53 binding sequence or the miR-192 promoter region. These components may include, but are not limited to, other nucleic acids, amino acids ligands, linkers, or other modification that will not effect the primary function of the inhibitory nucleic acid molecule in these embodiments, blocking the binding of p53 to the miR-192 promoter region and inhibiting the transcription of miR-192. For example, the inhibitor nucleic acid molecule may contain other nucleotides complementary to a position of the miR-192 promoter (SEQ ID NO:8) that it does not interact with the p53 binding sequence.

To effectively block the binding of p53 to the miR-192 promoter and the transcription of miR-192, the full sequence or complementary sequence of SEQ ID NOs:8 or 25 need not be utilized. A fragment of the sequence of complementary sequence would be adequate to block the binding of p53 to the miR-192 promoter and the transcription of miR-192. A suitable fragment can be at least 8, at least 10, at least 12, at least 14, at least 16, at least 18, at least 19, at least 20, at least 21, at least 22, at least 23, at least 24, or at least 25 nucleotides in length.

In Example 8 (see below), a three base pair gap between SEQ ID NO:25 and the p53 binding is discussed. Accordingly, 100% homology is not necessary. Instead, at least 85%, at least 90%, at least 92%, at least 94%, at least 95%, at least 96%, at least 97%, at least 98%, at least 99% or 100% homology is sufficient to enable the inhibitory nucleic acid molecule to bind to the miR-192 promoter or the p53 binding site.

In another embodiment, a non-viral approach may be employed for the introduction of an inhibitory nucleic acid molecule therapeutic to a cell of a patient diagnosed as having a neoplasia. For example, an inhibitory nucleic acid molecule that targets a miRNA-215 can be introduced into a cell by administering the nucleic acid in the presence of lipofection, asialoorosomucoid-polylysine conjugation, or by micro-injection under surgical conditions. In this embodiment, the inhibitory nucleic acid molecules are administered in combination with a liposome and protamine. Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell.

For any particular subject, the specific dosage regimes should be adjusted over time according to the individual need and the professional judgment of the person administering or supervising the administration of the compositions.

Methods of modulating expression of cellular components in an amount sufficient to modulate the cellular component are also provided. In embodiments, the cellular components may comprise miR-192 or miR-215, p21, p53, DHFR, TS or any cellular component regulated by these components. One of ordinary skill in the art would recognize that other cellular components may be modulated and are within the scope and spirit of this invention.

p53 and p21, a downstream target of the p53 pathway of growth control, are reported to block cells at G2 checkpoint mainly through inhibiting Cdc2 activity, the cyclin-dependent kinase that normally drives cells into mitosis, which is the ultimate target of pathways that mediate rapid arrest in G2 in response to DNA damage as reported in, for example, Taylor et al, "Regulation of the G2/M transition by p53", Oncogene. (2001); 20: 1803-1815; Stark et al., "Control of the G2/M transition," Mol. Biotechnol. (2006); 32: 227-248; and Bunz et al., "Requirement for p53 and p21 to sustain G2 arrest after DNA damage", Science. (1998); 282: 1497-1501.

Figure 6:
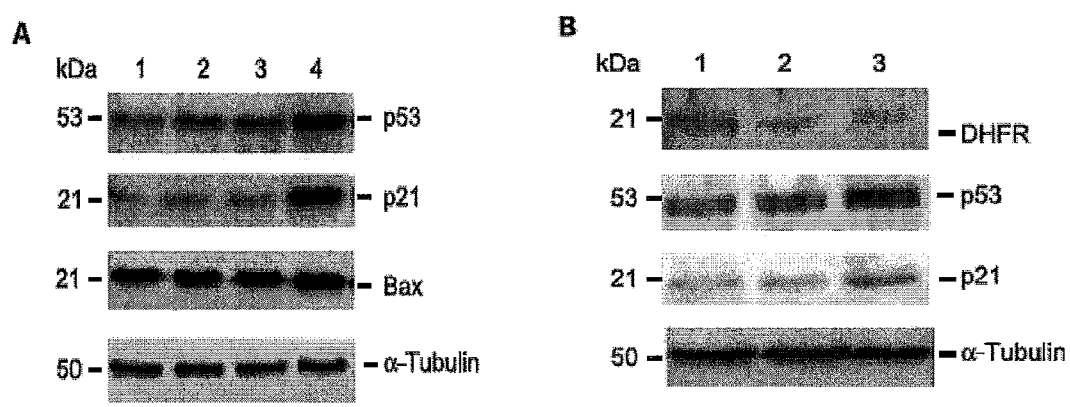
FIGS. 6A-B are images from a Western immunoblot of p53, p21 and Bax expression in HCT-116 (wt-p53) cells transfected with non-specific miR, DHFR siRNA or miR-192.
Figure 12:
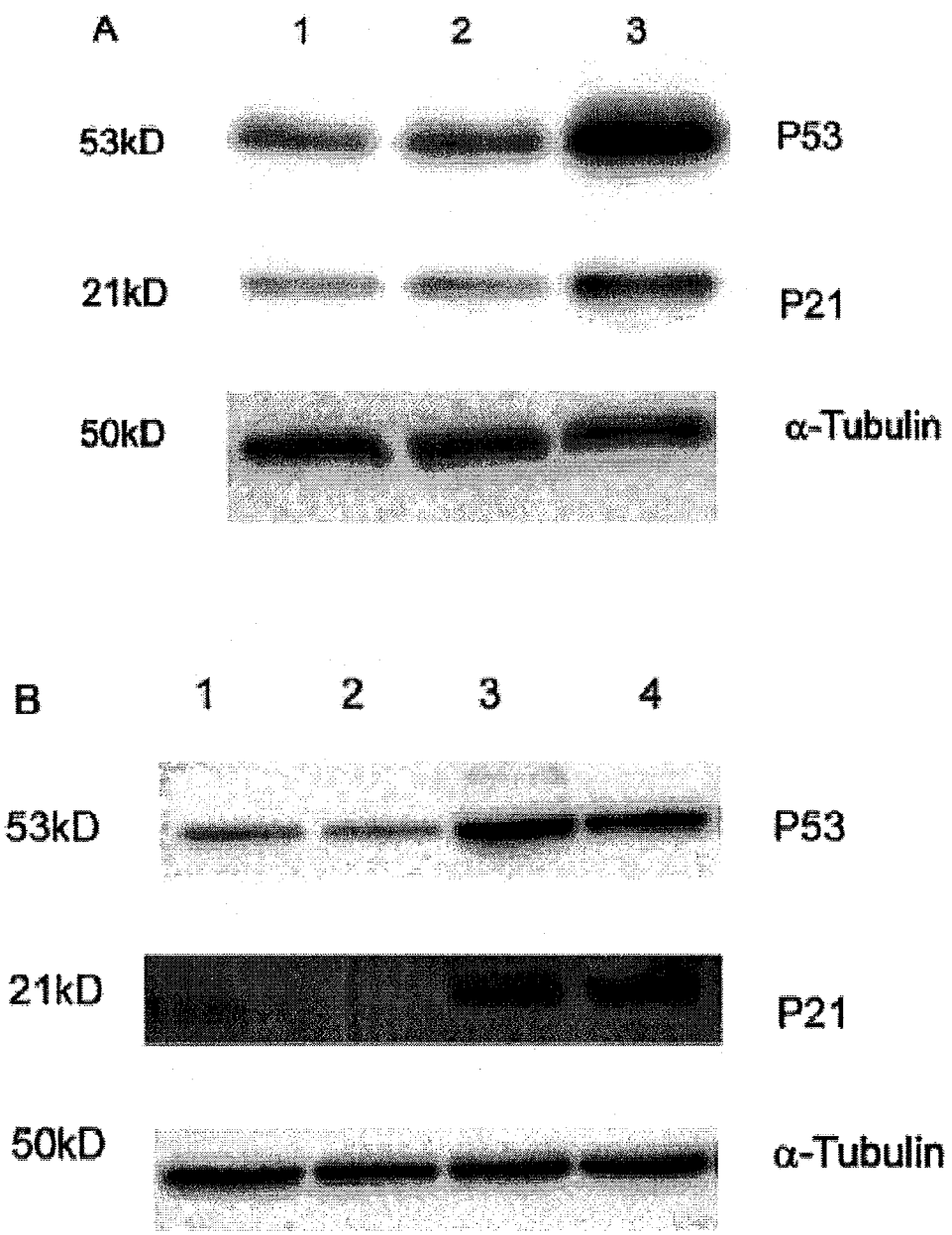
FIG. 12 depicts the levels of cell cycle control gene products p53 and p21 determined by Western immunoblot analysis.

The inventors have discovered that miR-192 or miR-215 can induce G2-arrest in HCT-116 (wt-p53) and U-2 OS cells. Transfection of miR-192 or miR-215 precursor into HCT-116 (wt-p53) and U-2 OS cells to analyze the mechanism of cell proliferation inhibition by miR-192 or miR-215 indicate that over-expression of miR-192 or miR-215 led to a significant increase of the p53 and p21 protein in both HCT-116 (wt-p53) and U-2 OS cells. FIGS. 6 and 12 depicts an evaluation of the levels of cell cycle control genes p53 and p21 by Western immunoblot analysis. As illustrated in FIGS. 6 and 12, miR-192 or miR-215 contributes to the inhibition of cell proliferation at least partially by the induction of G2-arrest in HCT-116 (wt-p53) and U-2 OS cells, which was through over-expression of G2-checkpoint genes p53 and p21.

Figure 14:
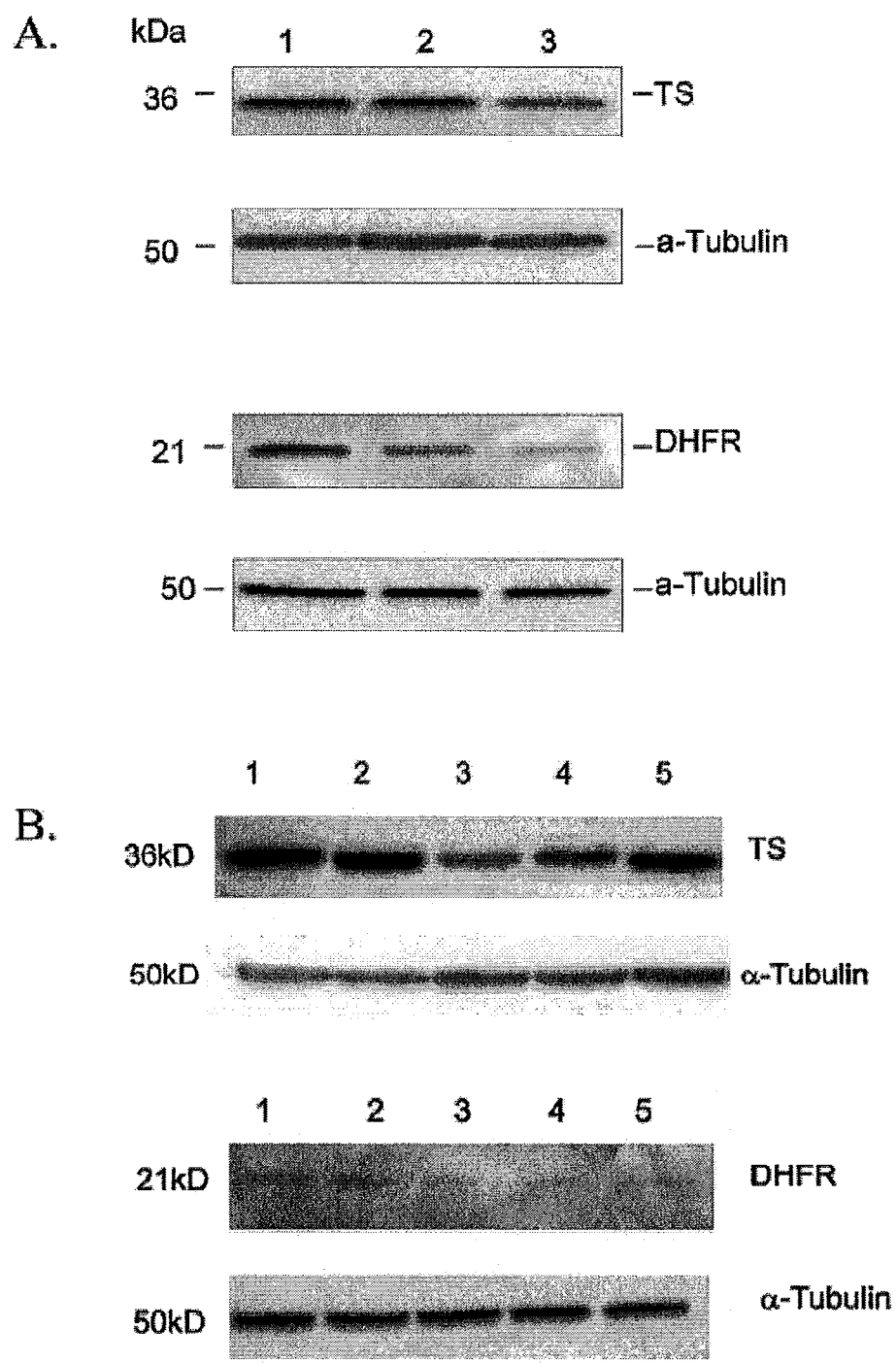
FIG. 14 depicts an analysis of levels of DHFR (Panel A) or TS (Panel B) protein in cells transfected with milt-215.
Figure 15:
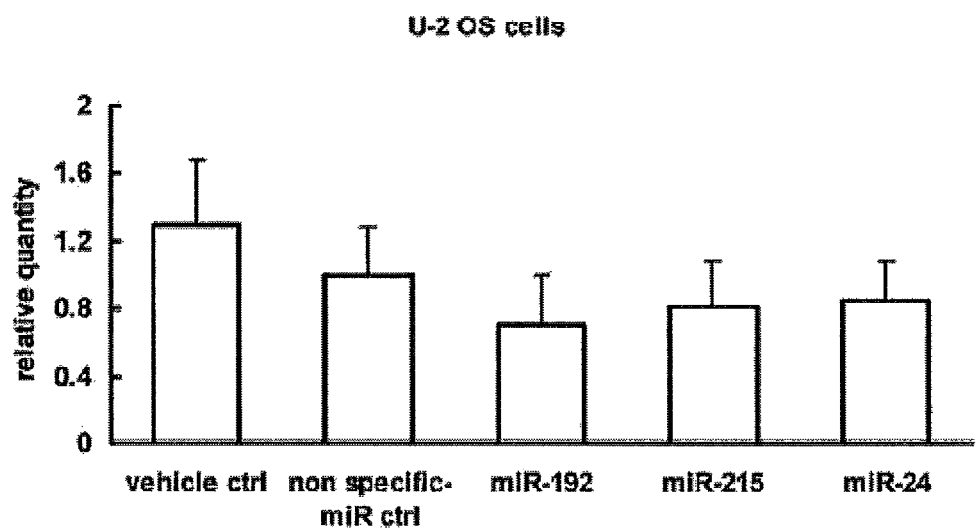
FIG. 15 depicts the levels of DHFR or TS mRNA in U-2 OS cells transfected with miR-215.

The inventors have discovered that miR-192 or miR-215 suppresses cell proliferation. Since most miRNAs have more than one target range from dozens to hundreds (see Wiemer, "The role of microRNAs in cancer: No small matter", Eur. J. Cancer. (2007) 43:1529-1544), miR-192 or miR-215 most likely targets the enzymes for DNA biosynthesis, such as TS and DHFR, and also leads to the inhibition of cell proliferation in cancer cells. As illustrated in FIG. 13, the inventors used the Sanger database (microrna.sanger.ac.uk) to identify TS and DHFR as the putative targets of miR-192 and miR-215. As illustrated in FIGS. 2 and 14, at 48 h after transfection, the inventors extracted the proteins and searched for the changes in TS or DHFR protein levels by Western immunoblot analysis. Oligofectamine alone and non-specific miRNA were used as the negative controls. The DHFR expression is down-regulated by miR-192. Using miR-192 as a positive control of DHFR down-regulation, the over-expression of miR-215 and miR-192 was confirmed by real time qRT-PCR analysis using U6 RNA to normalize the expression (see FIG. 11). Introduction of miR-192 or miR-215 clearly decreases TS or DHFR protein levels (see FIG. 2 and FIG. 14, lanes 3 and 4). The inventors also analyzed the expression level of TS or DHFR mRNA using real time qRT-PCR analysis. As illustrated in FIG. 15, the inventors discovered that there was no reduction in TS or DHFR mRNA expression by miR-192 or miR-215 (column 3) and miR-192 (column 4). Thus, the suppression of TS or DHFR expression was regulated at the translational level without the degradation of TS or DHFR mRNA.

In another embodiment, a method of increasing proliferation of a cell is provided using the mechanisms of the various pathways disclosed herein. In this embodiment, the cell is contacted with a nucleic acid complementary to at least a portion of miR-192 (SEQ ID NO:1), miR-215 (SEQ ID NO:9), an miR-192 promoter sequence that binds to p53 (SEQ ID NO:25) or the p53 sequence that binds to the miR-192 promoter. The amount of nucleic acid complementary to miR-192 (SEQ ID NO:1), miR-215 (SEQ ID NO:9), an miR-192 promoter sequence that binds to p53 (SEQ ID NO:25) or the p53 sequence that binds to the miR-192 promoter (SEQ ID NO:25) effective to increase proliferation of the cell is not particularly limited. In embodiments, the amount is in the range of more than about 20% for cell proliferation and more than about 2-fold of $IC_{50}$. In embodiments, the nucleic acid may comprise an antisense nucleic acid, siRNA or shRNA. In embodiments, the cell may comprise a cancer stem cell or a neoplastic cell.

In another embodiment, a method of increasing the sensitivity of a cell to a chemotherapeutic agent is provided using the mechanisms of the various pathways disclosed herein. In this embodiment, the cell is contacted with a nucleic acid complementary to at least a portion of miR-192 (SEQ ID NO:1), miR-215 (SEQ ID NO:9), an miR-192 promoter sequence that binds to p53 (SEQ ID NO:25) or the p53 sequence that binds to the miR-192 promoter (SEQ ID NO:25). The amount of nucleic acid complementary to miR-192, (SEQ ID NO:1), miR-215 (SEQ ID NO:9), an miR-192 promoter sequence that binds to p53 (SEQ ID NO:25) or the p53 sequence that binds to the miR-192 promoter effective to sensitize the cell to the chemotherapeutic agent is not particularly limited. In embodiments, the amount is in the range of more than about 20% for cell proliferation and more than about 2-fold of $IC_{50}$. In an embodiment, the chemotherapeutic agent is selected from the group consisting of a DHFA inhibitor and a TS inhibitor. Examples of chemotherapeutic agent include, but are not limited to, methotrexate (MTX), fluorouracil (5-FU), nolatrexed, ZD9331, GS7904L and raltitrexed (TDX). One of ordinary skill would recognize other chemotherapeutic agents useful in this embodiment. In embodiments, the nucleic acid may comprise an antisense nucleic acid, siRNA or shRNA. In embodiments, the cell may comprise a cancer stem cell or a neoplastic cell.

In another embodiment, a method of increasing the sensitivity of a cell to radiation is provided using the mechanisms of the various pathways disclosed herein. In this embodiment, the cell is contacted with a nucleic acid complementary to at least a portion of miR-192, (SEQ ID NO:1), miR-215 (SEQ ID NO:9), an miR-192 promoter sequence that binds to p53 (SEQ ID NO:25) or the p53 sequence that binds to the miR-192 promoter (SEQ ID NO:25). The amount of nucleic acid complementary to miR-192 (SEQ ID NO:1), miR-215 (SEQ ID NO:9), an miR-192 promoter sequence that binds to p53 (SEQ ID NO:25) or the p53 sequence that binds to the miR-192 promoter effective to sensitize the cell to radiation is not particularly limited. In embodiments, the amount is in the range of more than about 20% for cell proliferation and more than about 2-fold of $IC_{50}$. In embodiments, the nucleic acid may comprise an antisense nucleic acid, siRNA or shRNA. In embodiments, the cell may comprise a cancer stem cell or a neoplastic cell.

In still another embodiment, the compositions and methods of the present invention involve a first therapy an inhibitor of miR-192 or miR-215 or an expression construct encoding miR-192 or miR-215, used in combination with a second therapy to enhance the effect of the miR-192 or miR-215 therapy, or increase the therapeutic effect of the second therapy being employed to treat a neoplasm. These compositions would be provided in a combined amount effective to achieve the desired effect, such as the killing of a cancer cell and/or the inhibition of cellular hyperproliferation. This process may involve contacting the cells with the miR-192 or miR-215 and the second therapy at the same or different time. This may be achieved by contacting the cell with one or more compositions or pharmacological formulation that includes one or more of the agents, or by contacting the cell with two or more distinct compositions or formulations, wherein one composition provides (1) administering to the subject an effective amount of a nucleic acid molecule that inhibits expression of miR-192 or miR-215 and/or (2) a second therapy, in which the inhibition of expression of miR-192 or miR-215 sensitizes the neoplasm to the second therapy.

The second therapy may comprise administering chemotherapy, radiotherapy, surgical therapy, immunotherapy or gene therapy. In an embodiment, the chemotherapeutic agent is selected from the group consisting of a DHFR inhibitor and a TS inhibitor. The chemotherapeutic agents include, but are not limited to, DHFR inhibitors or TS inhibitors such as, for example, MTX, pemetrexed, 5-FU, raltitrexed (TDX), nolatrexed, ZD9331, and/or GS7904L. One of ordinary skill would recognize other chemotherapeutic agents useful in this embodiment. It is contemplated that the combination therapy may be provided in any suitable manner or under any suitable conditions readily apparent to one of ordinary skill in the art.

For example, administration of any compound or therapy of the present invention to a patient will follow general protocols for the administration of such compounds, taking into account the toxicity, if any, of the vector or any protein or other agent. Therefore, in some embodiments there is a step of monitoring toxicity that is attributable to combination therapy. It is expected that the treatment cycles would be repeated as necessary. It also is contemplated that various standard therapies, as well as surgical intervention, may be applied in combination with the described therapy.

A wide variety of other chemotherapeutic agents may be used in accordance with the present invention. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

In embodiments, the neoplasm being treated is a form of cancer. Cancers that may be evaluated by methods and compositions of the invention include any suitable cancer cells known to one of ordinary skill in the art. The inventors have found that the present invention is particularly useful in treating cancer cells from the colon or the pancreas, including pancreatic ductal adenocarcinoma. However, other suitable cells include cancer cells of the bladder, blood, bone, bone marrow, brain, breast, cervix, esophagus, gastrointestine, gum, head, kidney, liver, lung, nasopharynx, neck, ovary, prostate, rectum, skin, stomach, testis, tongue, or uterus. Other conditions treatable by the compositions and methods of the present invention will be readily apparent to one of ordinary skill in the art.

An inhibitory nucleic acid molecule of the invention, or other negative regulator of miR-192 or miR-215 may be administered within a pharmaceutically-acceptable diluent, carrier, or excipient, in unit dosage form. Conventional pharmaceutical practice may be employed to provide suitable formulations or compositions to administer the compounds to patients suffering from a neoplasia. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. Therapeutic formulations and methods for making such formulations are well known in the art.

The formulations can be administered to human patients in therapeutically effective amounts to provide therapy for a neoplastic disease or condition. The preferred dosage of inhibitory nucleic acid of the invention is likely to depend on such variables as the type and extent of the disorder, the overall health status of the particular patient, the formulation of the compound excipients, and its route of administration.

Therapy may be provided at any suitable location and under any suitable conditions. The duration of the therapy depends on various factors readily understood by one of ordinary skill in the art. Drug administration may also be performed at any suitable interval. For example, therapy may be given in predetermined on-and-off intervals as appropriate.

Depending on the type of cancer and its stage of development, the therapy can be used to slow the spreading of the cancer, to slow the cancer's growth, to kill or arrest cancer cells, to relieve symptoms caused by the cancer, or to prevent cancer. As described herein, if desired, treatment with an inhibitory nucleic acid molecule of the invention may be combined with therapies such as, for example, radiotherapy, surgery, or chemotherapy for the treatment of proliferative disease.

In another embodiment, a method of diagnosing a neoplasm in a subject is provided. In this embodiment, the method comprises determining the level of expression of miR-192 or miR-215.

As described herein, the present invention has identified increases in the expression of miR-192 or miR-215, and corresponding decreases in the expression of TS and DHFR that are associated with cellular proliferation. Alterations in the expression level of one or more of the following other markers used to diagnose a neoplasia are also contemplated. If desired, alterations in the expression of any combination of these markers is used to diagnose or characterize a neoplasia as would be readily apparent to one of ordinary skill in the art.

In an embodiment, a subject is diagnosed as having or having a propensity to develop a neoplasia, the method comprising measuring markers in a biological sample from a patient, and detecting an alteration in the expression of test marker molecules relative to the sequence or expression of a reference molecule. While the following approaches describe diagnostic methods featuring a miR-192 or miR-215, the skilled artisan will appreciate that any one or more of the markers set forth above is useful in such diagnostic methods. Increased expression of a miR-192 or miR-215 is correlated with neoplasia. Accordingly, the invention provides compositions and methods for identifying a neoplasia in a subject. The present invention provides a number of diagnostic assays that are useful for the identification or characterization of a neoplasia. Alterations in gene expression are detected using methods known to the skilled artisan and described herein. Such information can be used to diagnose a neoplasia.

In an embodiment, diagnostic methods of the invention are used to assay the expression of miR-192 or miR-215 in a biological sample relative to a reference sample. In one embodiment, the level of miR-192 or miR-215 is detected using a nucleic acid probe that specifically binds at least a portion of miR-192 (SEQ ID NO:1) or miR-215 (SEQ ID NO:9). Exemplary nucleic acid probes that specifically bind miR-192 or miR-215 are described herein. The biological sample can be any sample commonly used within the art, such as, for example, blood, urine, tissue or other bodily fluid.

In an embodiment, quantitative PCR methods are used to identify an increase in the expression of miR-192 or miR-215. In another embodiment, PCR methods are used to identify an alteration in the sequence of miR-192 or miR-215. The invention provides probes that are capable of detecting miR-192 or miR-215. Such probes may be used to hybridize to a nucleic acid sequence derived from a patient having a neoplasia. The specificity of the probe determines whether the probe hybridizes to a naturally occurring sequence, allelic variants, or other related sequences. Hybridization techniques may be used to identify mutations indicative of a neoplasia or may be used to monitor expression levels of these genes.

In embodiments, a measurement of a nucleic acid molecule in a subject sample may be compared with a diagnostic amount present in a reference. Any significant increase or decrease in the level of test nucleic acid molecule or polypeptide in the subject sample relative to a reference may be used to diagnose a neoplasia. Test molecules include any one or more of markers disclosed herein. In an embodiment, the reference is the level of test polypeptide or nucleic acid molecule present in a control sample obtained from a patient that does not have a neoplasia. In another embodiment, the reference is a baseline level of test molecules present in a biologic sample derived from a patient prior to, during, or after treatment for a neoplasia. In yet another embodiment, the reference can be a standardized curve. The subject sample can be any sample commonly used within the art, such as, for example, blood, urine, tissue or other bodily fluid.

In another embodiment, a method of identifying a neoplasm resistant to chemotherapy is provided. In this embodiment, the method comprises determining the level of expression in the neoplasm of miR-192 or miR-215, and identifying the neoplasm as resistant to therapy if the level of miR-192 or miR-215 is elevated, or identifying the neoplasm as not resistant to therapy if the level of miR-192 or miR-215 is reduced.

In another embodiment, a method of determining whether a neoplasm is a candidate for treatment with a chemotherapeutic agent is provided. In this embodiment, the method comprises evaluating the level of expression of miR-192 or miR-215 and rejecting the candidate if expression of the miR-192 or miR-215 is elevated, or accepting the candidate if the expression of miR-192 or miR-215 is reduced.

In another embodiment, a kit for analysis of a pathological sample is provided. Any of the compositions described herein may be comprised in the kit. In a non-limiting example, reagents for isolating miRNA, labeling miRNA, and/or evaluating a miRNA population using an array, nucleic acid amplification, and/or hybridization can be included in a kit, as well as reagents for preparation of samples from blood samples. The kit may further include reagents for creating or synthesizing miRNA probes. The kits may comprise, in suitable container means, an enzyme for labeling the miRNA by incorporating labeled nucleotides or unlabeled nucleotides that are subsequently labeled. In certain aspects, the kit can include amplification reagents. In other aspects, the kit may include various supports, such as glass, nylon, polymeric beads, and the like, and/or reagents for coupling any probes and/or target nucleic acids. It may also include one or more buffers, such as a reaction buffer, labeling buffer, washing buffer, or a hybridization buffer, compounds for preparing the miRNA probes, and components for isolating miRNA. Other kits of the invention may include components for making a nucleic acid array comprising miRNA, and thus, may include, for example, a solid support. The pathological sample can be any sample commonly used within the art, such as, for example, blood, urine, tissue or other bodily fluid.

Kits for implementing methods of the invention described herein are specifically contemplated. In some embodiments, there are kits for preparing miRNA for multi-labeling and kits for preparing miRNA probes and/or miRNA arrays. In these embodiments, the kit may comprise, in suitable container means, any suitable solvents, buffers, reagents, or additives known to one of ordinary skill in the art including, but not limited to, those generally used for manipulating RNA, such as formamide, loading dye, ribonuclease inhibitors, and DNase.

In other embodiments, kits may include an array containing miRNA probes. Such arrays may include, for example, arrays relevant to a particular diagnostic, therapeutic, or prognostic application. For example, the array may contain one or more probes that is indicative of a disease or condition, susceptibility or resistance to a drug or treatment, susceptibility to toxicity from a drug or substance, prognosis, and/or genetic predisposition to a disease or condition.

For any kit embodiment, including an array, there can be nucleic acid molecules that contain or can be used to amplify a sequence that is a variant of identical to or complementary to all or part of any SEQ ID described herein. In certain embodiments, a kit or array of the invention can contain one or more probes for the miRNAs identified by the SEQ IDs described herein. Any nucleic acid discussed above may be implemented as part of a kit.

The components of the kits may be packaged in any suitable manner known to one of ordinary skill in the art such as, for example, in aqueous media or in lyophilized form. The kits of the present invention may also include a means for containing the nucleic acids, and any other reagent containers in close confinement for commercial sale. Such containers may include injection or blow molded plastic containers into which the desired vials are retained.

In this embodiment, the kits may also include components that facilitate isolation of the labeled miRNA. It may also include components that preserve or maintain the miRNA or that protect against its degradation. Such components may be RNAse-free or protect against RNAses. Such kits generally will comprise, in suitable means, distinct containers for each individual reagent or solution.

A kit will also include instructions for employing the kit components as well as the use of any other reagent not included in the kit. Instructions may include variations that can be implemented.

In another embodiment, a method of identifying an agent that inhibits the expression or activity of miR-192 or miR-215 is provided. In embodiments, the method comprises contacting a cell that expresses the miR-192 or miR-215 with an agent, and comparing the expression level of the miR-192 or miR-215 in the cell contacted by the agent with the expression level of the miR-192 or miR-215 in the absence of the agent. According to this embodiment, the agent is an inhibitor of the miR-192 or miR-215 if expression of the miR-192 or miR-215 is reduced. In this embodiment, the test cell may overexpress the miRNA.

Compounds that modulate the expression or activity of a miR-192 or miR-215 are useful in the methods of the invention for the treatment, prevention, diagnosis and prognostication of a neoplasm or subject. The method of the invention may measure a decrease in transcription of miR-192 or miR-215 or an alteration in the transcription or translation of the target of miR-192 or miR-215. Any number of methods are available for carrying out screening assays to identify such compounds. In an embodiment, the method comprises contacting a cell that expresses miR-192 or miR-215 with an agent and comparing the level of miR-192 or miR-215 expression in the cell contacted by the agent with the level of expression in a control cell, wherein an agent that decreases the expression of miR-192 or miR-215 thereby, in combination with a secondary therapy, inhibits a neoplasia. In another embodiment, candidate compounds are identified that specifically bind to and alter the activity of miR-192 or miR-215 of the invention. Methods of assaying such biological activities are known in the art. The efficacy of such a candidate compound is dependent upon its ability to interact with miR-192 or miR-215. Such an interaction can be readily assayed using any number of standard binding techniques and functional assays.

Potential agonists and antagonists of miR-192 or miR-215 include, but are not limited to, organic molecules, peptides, peptide mimetics, polypeptides, nucleic acid molecules, and antibodies that bind to a nucleic acid sequence of the invention and thereby inhibit or extinguish its activity. Potential antagonists also include small molecules that bind to miR-192 or miR-215 thereby preventing binding to cellular molecules with which the miR-192 or miR-215 normally interacts, such that the normal biological activity of miR-192 or miR-215 is reduced or inhibited. Small molecules of the invention preferably have a molecular weight below 2,000 daltons, more preferably between 300 and 1,000 daltons, and still more preferably between 400 and 700 daltons. It is preferred that these small molecules are organic molecules.

The invention also includes novel compounds identified by the above-described screening assays. These compounds are characterized in one or more appropriate animal models to determine the efficacy of the compound for the treatment of a neoplasia. Characterization in an animal model can also be used to determine the toxicity, side effects, or mechanism of action of treatment with such a compound. Furthermore, novel compounds identified in any of the above-described screening assays may be used for the treatment of a neoplasia in a subject. Such compounds are useful alone or in combination with other conventional therapies known in the art.

It is also contemplated that the invention can be used to evaluate differences between stages of disease, such as between hyperplasia, neoplasia, precancer and cancer, or between a primary tumor and a metastasized tumor. Moreover, it is contemplated that samples that have differences in the activity of certain pathways may also be compared. It is further contemplated that nucleic acids molecules of the invention can be employed in diagnostic and therapeutic methods with respect to any of the above pathways or factors. Thus, in some embodiments of the invention, a miRNA may be differentially expressed with respect to one or more of the above pathways or factors. The samples can be any sample commonly used within the art, such as, for example, blood, urine, tissue or other bodily fluid.

In certain embodiments, miRNA profiles may be generated to evaluate and correlate those profiles with pharmacokinetics. For example, miRNA profiles may be created and evaluated for patient tumor and blood samples prior to the patient's being treated or during treatment to determine if there are miRNAs whose expression correlates with the outcome of the patient. Identification of differential miRNAs can lead to a diagnostic assay involving them that can be used to evaluate tumor and/or blood samples to determine what drug regimen the patient should be provided. In addition, it can be used to identify or select patients suitable for a particular clinical trial. If a miRNA profile is determined to be correlated with drug efficacy or drug toxicity, that may be relevant to whether that patient is an appropriate patient for receiving the drug or for a particular dosage of the drug. One of ordinary skill in the art would recognize that other samples, such as urine, bodily fluid or tissue, can also be used.

In addition to the above prognostic assay, samples from patients with a variety of diseases can be evaluated to determine if different diseases can be identified based on blood miRNA levels. A diagnostic assay can be created based on the profiles that doctors can use to identify individuals with a disease or who are at risk to develop a disease. The samples may be any sample commonly taken from a patient, such as, for example, blood, urine or tissue. Alternatively, treatments can be designed based on miRNA profiling.

All references mentioned herein are incorporated in their entirety by reference into this application.

It is to be understood and expected that variations in the principles of the invention herein disclosed may be made by one skilled in the art and it is intended that such modifications are to be included within the scope of the present invention. The following examples only illustrate particular ways to use the novel technique of the invention, and should not be construed to limit the scope of the invention in any way.

Example 1 miR-192 regulates the expression of DHFR. There are several miRNAs that potentially interact with the 3'-UTR region of DHFR mRNA. Bioinformatic analysis of the secondary structure of the 3'-UTR of the DHFR mRNA and miRNA binding sites reduced the candidate miRNAs to a small number. From this analysis, miR-192 was identified as a candidate that may regulate DHFR.

Figure 1A:
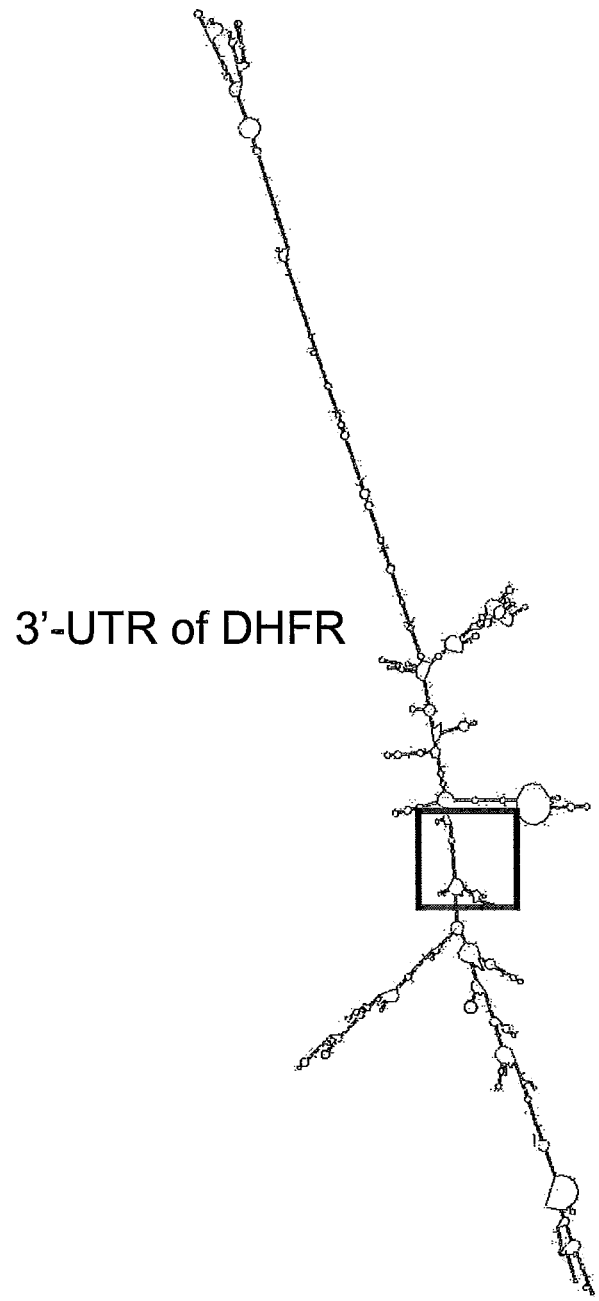
FIG. 1 depicts a predicted secondary structure of the interaction between miR-192 and the 3'-UTR region of DHFR mRNA.

FIG. 1 shows the secondary structure of the 3'-UTR of the DHFR mRNA and the target sequence that interacts with miR-192. To experimentally confirm the expression of DHFR was regulated by miR-192, a miR-192 precursor was transfected into HCT-116 (wt-p53) cells. A non-specific miR was used as a negative control. It has been reported that the expression of DHFR is regulated by miR-24. A DHFR siRNA and miR-24 were used as positive controls. Over-expression of miR-192 (FIG. 2A) and miR-24 (FIG. 2B) was confirmed by real time qRTPCR analysis using U6 RNA to normalize the expression.

Figure 2A:
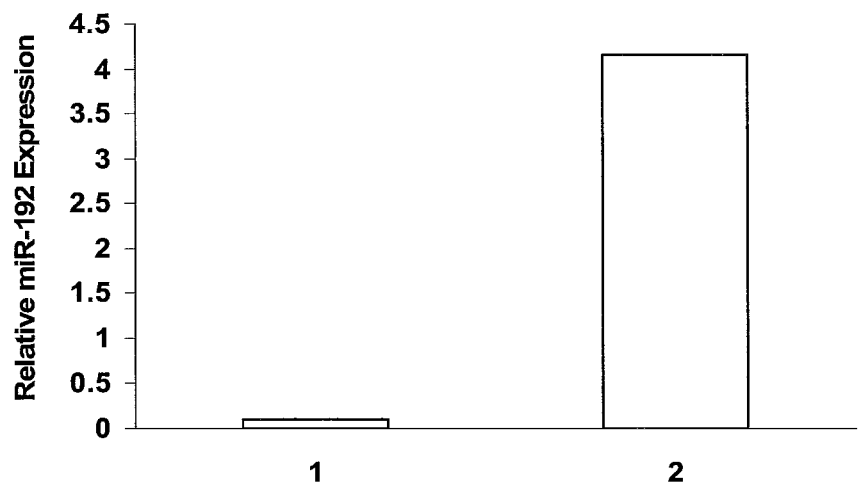
FIG. 2A is a graph illustrating the expression of miR-192 in HCT-116 (wt-p53) cells transfected with miR-192.
Figure 2B:
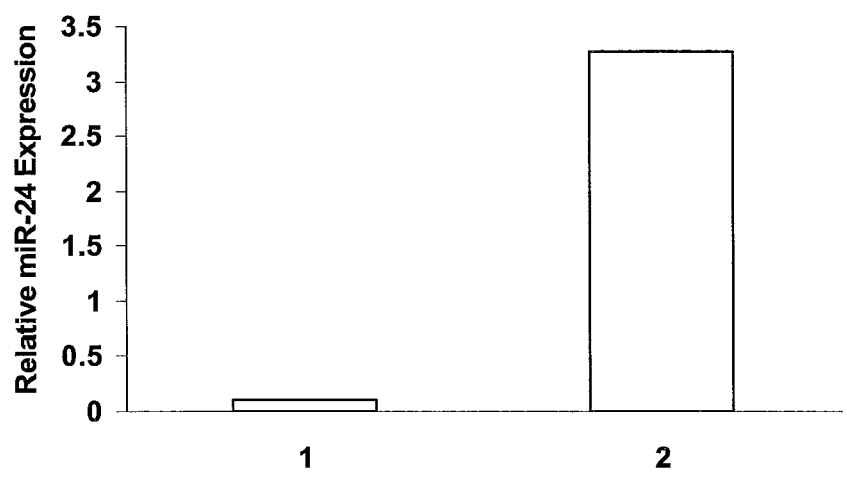
FIG. 2B is a graph illustrating the expression of miR-24 in HCT-116 (wt-p53) cells transfected with miR-24.
Figure 2C:
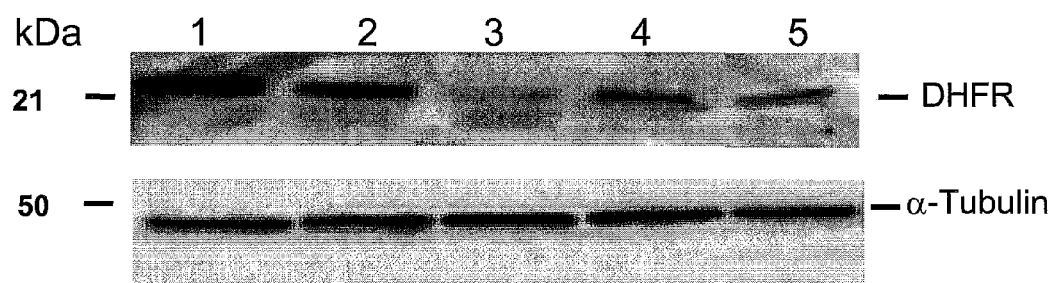
FIG. 2C depicts an image from a Western immunoblot showing the expression of DHFRT protein in HCT-116 (wt-p53) cells transfected with DHFR specific siRNA, miR-192 or miR-24.

The expression of DHFR protein was analyzed using Western immunoblot analysis and the results are shown in FIG. 2C. In this experiment, human colon cancer cell lines, HCT-116 (wt-p53), cells were transfected with miR-192 or miR-24. The cells were maintained in McCoy's 5A medium (Life Technologies). The media was supplemented with 10% dialyzed fetal bovine serum (Hyclone Laboratories). The cell line were grown at 37° C. in a humidified incubator with 5% $CO_2$.

The HCT-116 (wt-p53) cells tranfected as follows. The cells ($2\times10^5$) were plated in 6-well plates and transfected with 100 nmol/L of either miR-192 or miR-24 precursors or non-specific control miR (Ambion) after 24 h with Oligofectamine (Invitrogen) according to the manufacturer's instructions. Small interfering RNA (siRNA) specific to DHFR (On-Target plus SMARTpool L-008799-00-0010, human DHFR, NM_000791) (Dharmacon) and transfected with Oligofectamine (Invitrogen) according to the manufacturer's protocols at a final concentration of 100 nmol/L. siRNA specific to DHFR was used as the positive control, miR-24, a miRNA that also targets DHFR (Mishra, et al., "A miR-24 microRNA binding site polymorphism in dihydrofolate reductase gene leads to methotrexate resistance: Prof. Nat'l. Acad. Sci. (2007) 104:13513-13518) was also used as a positive control.

At 48 hours after transfection with miR-192 or miR-24 precursors or nonspecific control miRNA, the cells were scraped and lysed in radioimmunoprecipitation assay buffer (Sigma). Equal amount of proteins were resolved by SDS-PAGE on 12% gels by the method of Laemmli, "Cleavage of structured proteins during the assemble of the head of bacteriophase 74," Nature (1970) 227:680-685, and transferred to polyvinylidene difluoride membranes (Bio-Rad Laboratories). The membranes were then blocked by 5% nonfat milk in TBS-0.5% Tween 20 at room temperature for 1 hour. The primary antibodies used for the analysis included mouse anti-DHFR monoclonal antibody (mAb; 1:250; BD Biosciences), and mouse anti-α-tubulin mAb (1:1,000; TU-02) (Santa Cruz Biotechnology). Horseradish peroxidase-conjugated antibodies against mouse or rabbit (1:1,000; Santa Cruz Biotechnology) were used as the secondary antibodies. Protein bands were visualized with a chemiluminescence detection system using the Super Signal substrate.

FIG. 2C is the resulting Western immunoblot that shows overexpression of miR-192 clearly decreased the expression of DHFR protein (FIG. 2C, lane 4). In this image, lane 1 is the control, lane 2 is the cells transfected with non-specific miR control, lane 3 is the cells transfected with siRNA specific to DHFR, lane 4 is from cells transfected with miR-192 and lane 5 is the cells transfected with miR-24. The results show that the potency of miR-192 (FIG. 2C, lane 4) for decreasing DHFR expression was comparable to miR-24 (FIG. 2C, lane 5).

The expression level of DHFR mRNA were analyzed using real time qRT-PCR analysis. The analysis was performed as follows. Total RNA, including miRNA, was isolated from cell lines by using TRIzol reagent (Invitrogen) according to the manufacturer's instructions at 24 h after transfection. cDNA was synthesized with the High Capacity cDNA synthesis kit (Applied Biosystems) using 2 μg of total RNA as the template and random primers. Real-time qRT-PCR analysis was done on the experimental mRNAs. The PCR primers and probes for DHFR, and the internal control gene GAPDH were purchased from Applied Biosystems. qRT-PCR was done on an ABI 7500HT instrument under the following conditions: 50° C., 2 min of reverse transcription; 95° C., 10 min; 95° C., 15 sec; 60° C., 1 min. The reaction was done for up to 40 cycles (n=3). GAPDH was used as an internal standard for normalization.

Figure 2D:
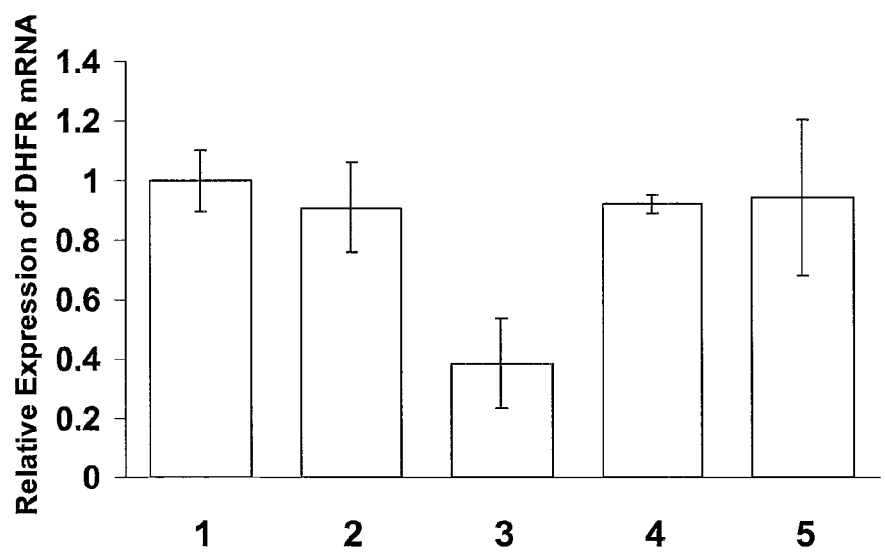
FIG. 2D is a graph illustrating the expression of DHFR mRNA in HCT-116 (wt-p53) cells transfected with DHFR specific siRNA, miR-192 or miR-24.

The results (FIG. 2D) indicated that there was no reduction in DHFR mRNA expression by miR-192 (lane 4) and miR-24 (lane 5). In FIG. 2D, each bar corresponds to each lane illustrated in FIG. 2C (see above). The results demonstrate that the suppression of DHFR expression was regulated at the translational level without the degradation of DHFR mRNA. By contrast, the decreased expression of DHFR by siRNA was clearly caused by mRNA degradation (lane 3, FIG. 2D).

Example 2

Figure 3:
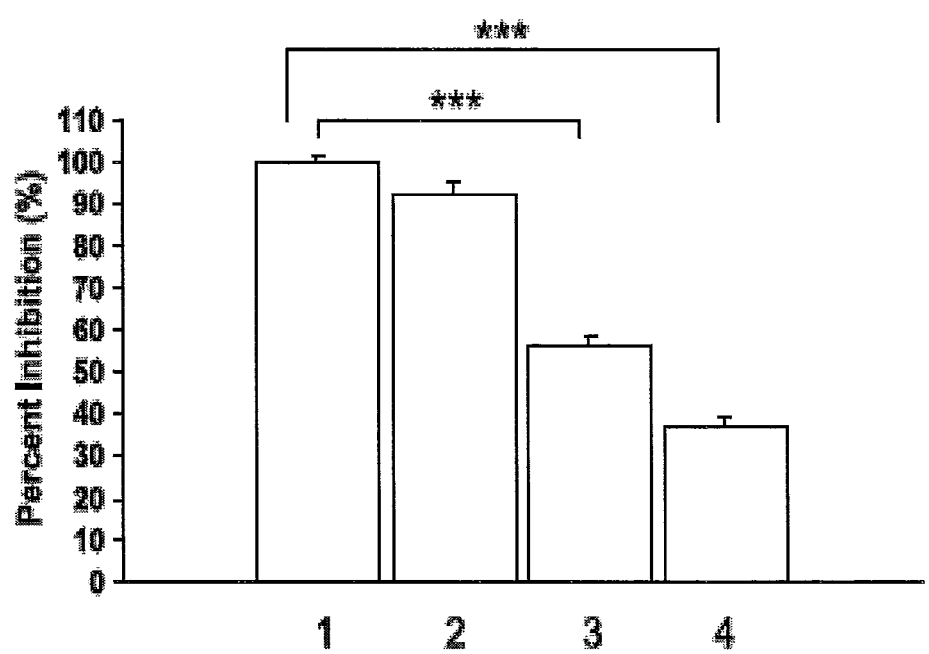
FIG. 3 is a graph illustrating the impact of miR-192 on cell proliferation with MTX treatment in HCT-116 (wt-p53) cells transfected with DHFR specific siRNA or miR-192.

Increased expression of miR-192 sensitizes cells to Methotrexate (MTX) treatment. This was confirmed by studying cellular proliferation in cells transfected with miR-192 and treated with MTX. HCT-116 (wt-p53) cells were plated in 96-well plates at 1×10³ cells/well in triplicate. They were transfected with miR-192 precursor (FIG. 3, lane 4), non-specific control miRNA (FIG. 3, lane 2), or siRNA against DHFR (FIG. 3, lane 3) in 100 µl of medium. Twenty-four hours later, MTX in 100 µl medium (final concentration 25 nM) was added, and incubated for 72 hours. One sample was only transfected with non-specific miR and was not treated with MTX (FIG. 3, lane 1). Ten microliters of WST-1 (Roche Applied Science) was added to each well. After 2 hours of incubation, absorbance was measured at 450 and 630 nm respectively (n=3). Non-specific control miRNA alone was used as a negative control (FIG. 3, lane 1), and siRNA incubation with MTX was used as a positive control (FIG. 3, lane 3).

With equal molar concentration of MTX at 25 nM (IC-10), cell proliferation was reduced by 10% in non specific control miR treated cells (FIG. 3, lane 2). However, cell proliferation was reduced by nearly 70% in cells transfected with miR-192, demonstrating a synergistic effect in combination with MTX (FIG. 3, lane 4). By contrast, cells treated with siRNA against DHFR were inhibited by 55% (FIG. 3, lane 3). The more potent effect of miR-192 plus MTX compared to siRNA targeting specifically to DHFR suggests that miR-192 may also target additional mRNA targets through imperfect base pairing.

Example 3 miR-192 inhibits cell proliferation of HCT-116 (wt-p53), RKO (wt-p53) and HT-29 (mut-p53) colon cancer cell lines. To assess the functional significance of miR-192, the impact of miR-192 on cellular proliferation was evaluated using HCT-116 (wt-p53), HCT-116 (null-p53), RKO (wt-p53) and HT-29 (mut-p53) colon cancer cell lines. The human colon cancer cell lines HCT-116 (wt-p53) and HCT-116 (null-p53) were provided by Prof Bert Vogelstein (The Johns Hopkins University) and were maintained in McCoy's 5A medium (Life Technologies). The other two human colon cancer cell lines, RKO (wt-p53) and HT-29 (mut-p53), were obtained from the American Type Culture Collection. The HT-29 (mut-p53) cell line has a missense mutation in codon 273 of p53 resulting in an Argto-His substitution. RKO (wt-p53) and HT-29 (mut-p53) cells were maintained in Eagle's MEM and Iscove's Modified Dulbecco's Medium at the American Type Culture Collection, respectively. All media were supplemented with 10% dialyzed fetal bovine serum (Hyclone Laboratories). All cell lines were grown at 37° C. in a humidified incubator with 5% $CO_2$. The cell lines were transfected as described above (see Examples 1 and 2).

Figure 4A:
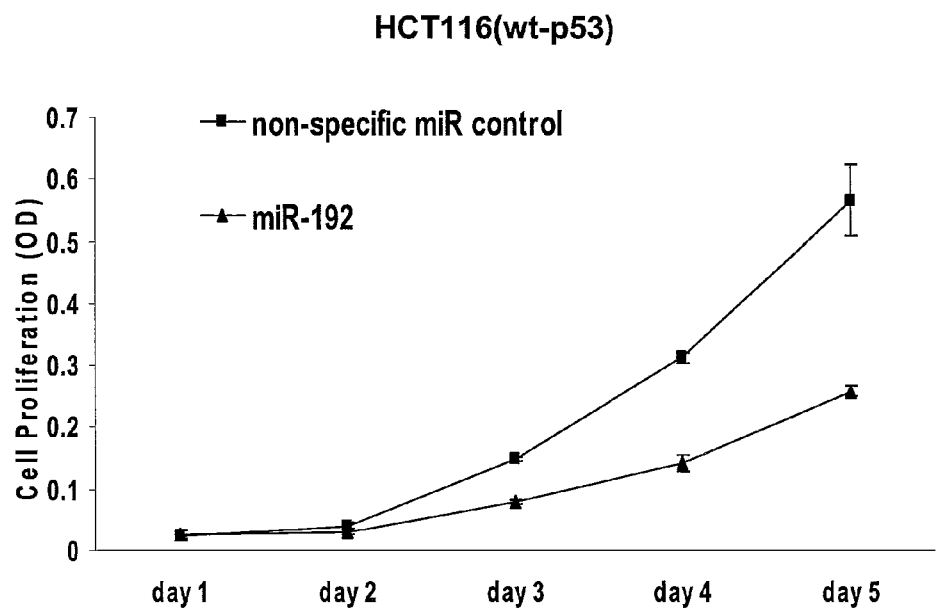
FIGS. 4A-D is a graph illustrating the impact of miR-192 on cell proliferation in HCT-116 (wt-p53) cells (FIG. 4A), RKO cells (FIG. 4B), HCT-116 (null-p53) cells (FIG. 4C) and HT-29 (FIG. 4D) cells transfected with non-specific miR or miR-192.
Figure 4B:
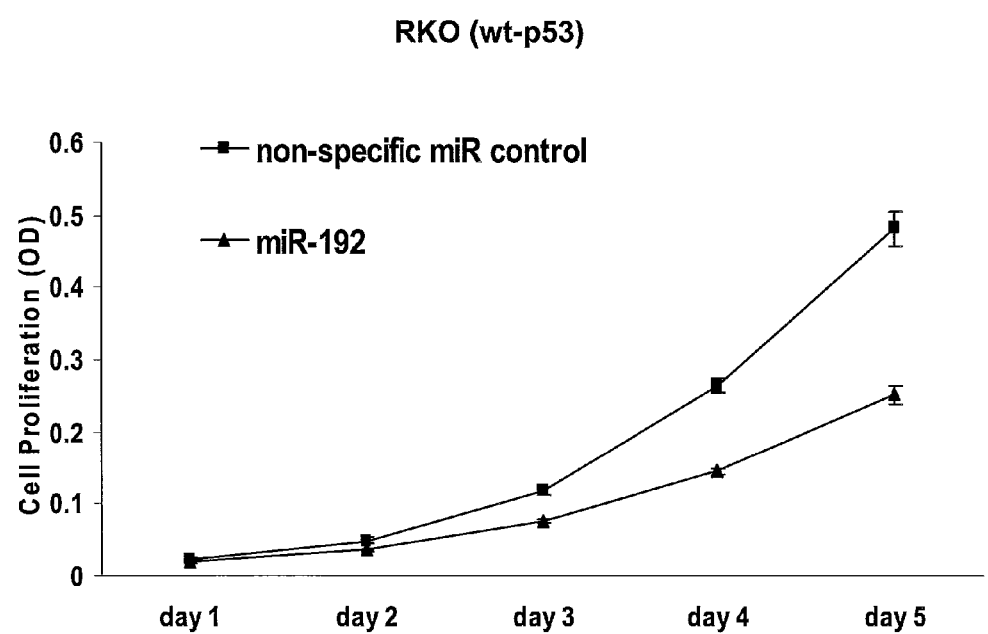
Figure 4C:
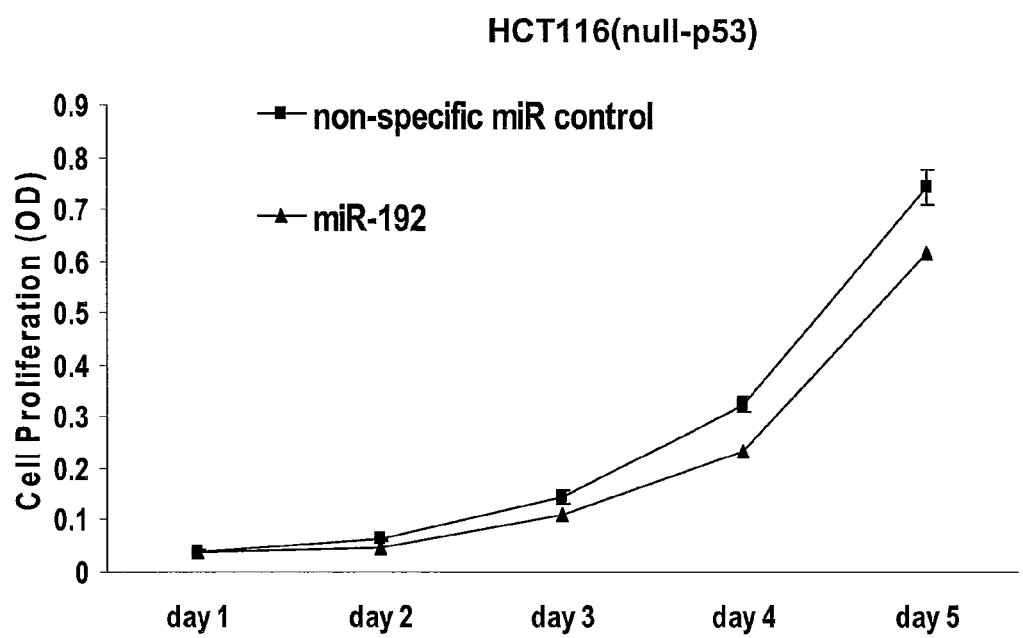

The cellular proliferation was evaluated as follows. HCT-116 (wt-p53) (FIG. 4A), HCT-116 (null-p53) (FIG. 4C), RKO (wt-p53) (FIG. 4B), and HT-29 cells (FIG. 4D) were plated in 96-well plates in triplicate at 1×10³ cells per well after transfection with miR-192 precursor (illustrated as—Δ—) or non-specific control miRNA (illustrated as—☐—). Cells were cultured for 24, 48, 72, or 96 hours. The absorbance at 450 and 630 nm was measured after incubation with 10 µl of WST-1 for 2 hours. A non-specific miR was used as a negative control.

Figure 4D:
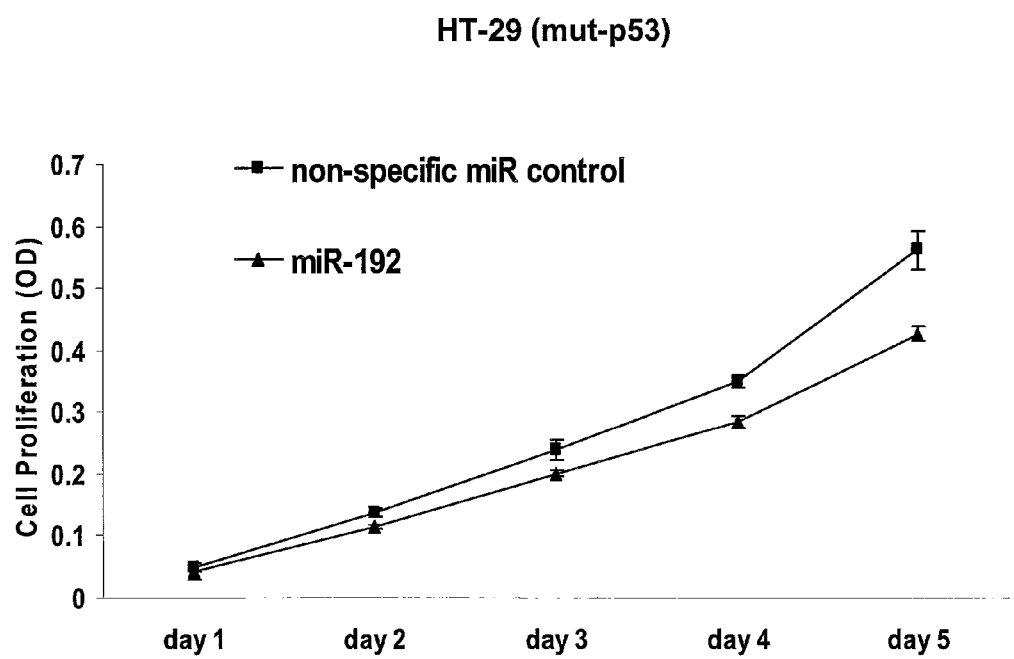

The results (see FIG. 4) show that the overexpression of miR-192 can suppress cellular proliferation in HCT-116 (wt-p53) cells by over 55% (n=3) (FIG. 4A) and RKO (wt-p53) cells by 48% (n=3) (FIG. 4B), with less impact on HCT-116 (null-p53) (15%, n=3) (FIG. 4C) and HT-29 cell lines (24%, n=3) (FIG. 4D). By contrast, the non-specific control miR has no effect on cellular proliferation, indicating that this effect caused by miR-192 is highly specific. The results clearly showed that the effect of miR-192 on the inhibition of cellular proliferation is more potent in colon cancer cells containing wild type p53, further indicating that miR-192's function depends on the status of p53.

Example 4

To determine whether the miR-192's impact on cellular proliferation was related to cell cycle control, the effect on cell cycle control was analyzed by flow cytometry using HCT-116 (wt-p53) (FIG. 5A) and HCT-116 (null-p53) (FIG. 5B) cells transfected with non-specific control miR (left line graph) or miR-192 (right line graph). This experiment was performed as follows. The HCT-116 (wt-p53) and HCT-116 (null-p53) cells lines as described above (see Example 3) were transfected with miR-192 precursor and the non-specific control miRNA described as above (see Examples 1 and 2). At 36 hours after transfection, the cells were harvested and resuspended at 0.5-1×10⁵ cells/ml in modified Krishan buffer containing 0.1% sodium citrate and 0.3% NP-40 and kept at 4° C. Before being analyzed by flow cytometry, cells were treated with 0.02 mg/ml RNase H and stained with 0.05 mg/ml propidium iodide (Sigma).

In the HCT-116 (wt-p53) cells transfected with non-specific miR had the following cell cycle profile G1: 38.78%, G2: 17.46%, S: 43.76%, G1/S: 0.89%, and G2/S: 0.40%. The HCT-116 (wt-p53) cells transfected with miR-192 had the follow cell cycle profile G1: 40.84%, G2: 44.71%, S: 14.45%, G1/S: 2.83%, and G2/S: 3.09%. In the HCT-116 (null) cells transfected with non-specific miR had the following cell cycle profile G1: 40.15%, G2: 13.33%, S: 46.52%, G1/S: 0.86%, and G2/S: 0.29%. The HCT-116 (null) cells transfected with miR-192 had the follow cell cycle profile G1: 35.65%, G2: 19.06%, S: 45.29%, G1/S: 0.79% and G2/S: 0.42%.

Figure 5A:
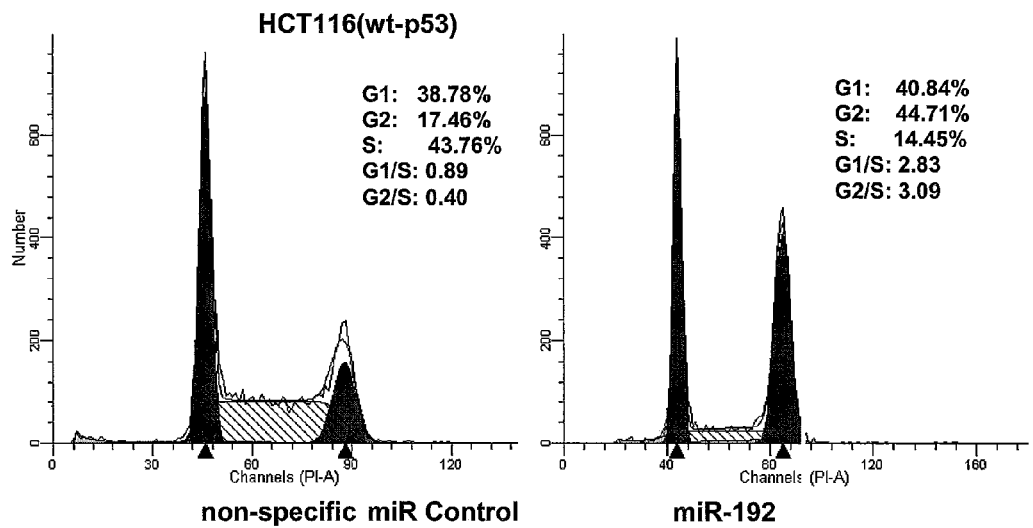
FIGS. 5A-B are graphs illustrating impact of miR-192 on cell proliferation in HCT-116 (wt-p53) (FIG. 5A) and HCT-116 (null-p53) (FIG. 5B) cells transfected with non-specific miR or miR-192.
Figure 5B:
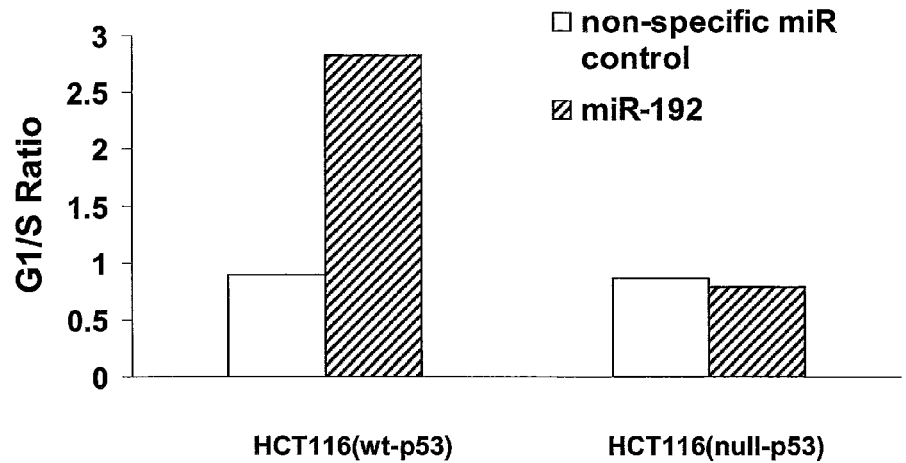
Figure 5C:
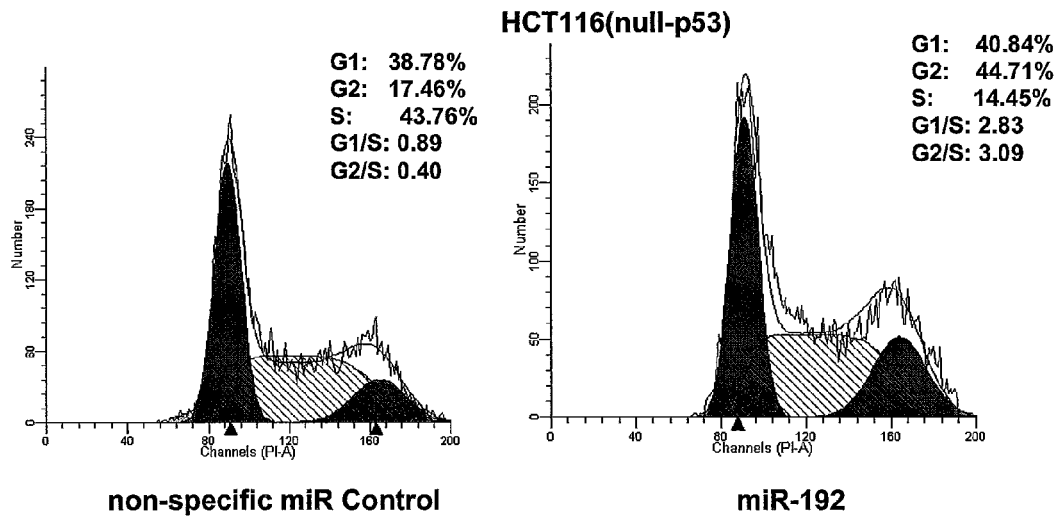
Figure 5D:
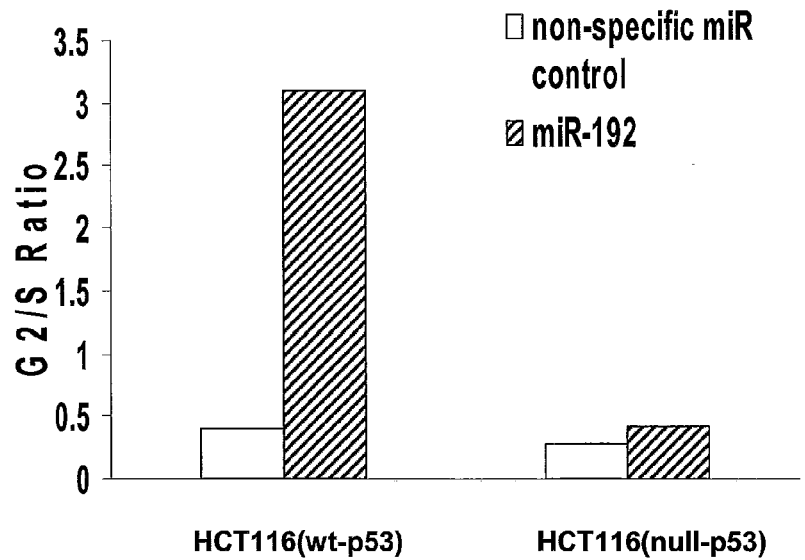

The results (FIG. 5) show that miR-192 induces both G1 (>2-fold) and G2 arrest (>3-fold) in HCT-116 (wt-p53) cells (FIG. 5A). By contrast, this effect has not been observed in HCT-116 (null-p53) cells (FIG. 5B). The cell cycle analysis data is highly consistent with the cell proliferation results that the function of miR-192 is dependent on the presence of wild type p53 for cell cycle control.

Example 5 miR-192 expression is dependent on p53. To further analyze the cell cycle control genes involved in miR-192 overexpression, a number of cell cycle control genes were analyzed (p53, p21, Bax, E2F3, Rb). HCT-116 (wt-p53) cells (FIG. 6A) and RKO (wt-p53) cells (FIG. 6B), as described above (see Example 3), were transfected with non-specific miR (FIG. 6A, lane 2; and FIG. 6B, lane 1), DHFR siRNA (FIG. 6A, lane 3; and FIG. 6B, lane 2) and miR-192 (FIG. 6A, lane 4; and FIG. 6B, lane 3) according to the procedure discussed above (see Examples 1 and 2). Non-transfected HCT-116 (wt-p53) was used as a negative control (FIG. 6A, lane 1). Alpha-tubulin was used as a protein loading control. At 48 hours after transfection, the cells were scraped and lysed in RIPA buffer (Sigma). Equal amount of proteins were resolved by SDS-PAGE on 12% gels by the method of Laemmli, and transferred to polyvinylidene fluoride membranes (BIO-RAD Laboratories). The membranes were then blocked by 5% nonfat milk in TBS-T (Tris-buffered saline and 0.5% Tween-20) at room temperature for 1 hour. The primary antibodies used for the analysis included mouse anti-p53 mAb (1:1000, DO-1) (Santa Cruz Biotechnology), mouse anti-p21 mAb (1:1000, F-5) (Santa Cruz Biotechnology), and mouse anti-α-tubulin mAb (1:1000, TU-02) (Santa Cruz Biotechnology). Horseradish peroxidase—conjugated antibodies against mouse or rabbit (1:1000) (Santa Cruz Biotechnology) were used as the secondary antibodies. Protein bands were visualized with a chemiluminescence detection system using the Super Signal substrate.

FIG. 6 shows the results of Western immunoblot analysis in HCT-116 (wt-p53) 10 cells (FIG. 6A) and RKO (wt-p53) cells (FIG. 6B). miR-192 increased the expression of the p53 protein (FIG. 6A, lane 4) over 10-fold and p21 10-fold. By contrast, siRNA against DHFR (FIG. 6A, lane 3) did not cause an increase in expression of p53 and p21. The expression of Bax was not altered by miR-192. Similar results were obtained for RKO (wt-p53) cells (FIG. 6B, lane 3 (miR-192), lane 1 (non-specific miR) and lane 2 (siRNA of DHFR)).

Example 6

Figure 7:
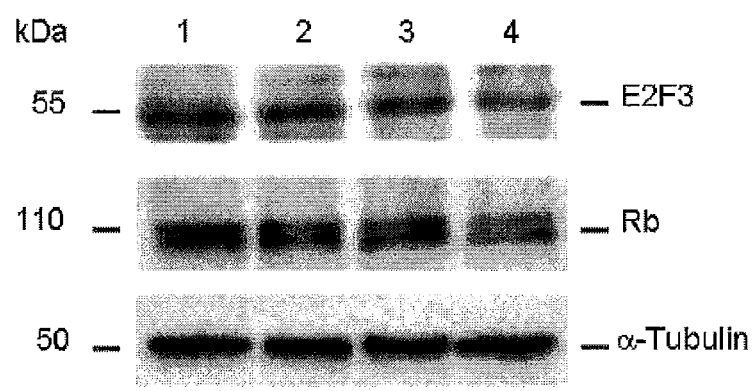
FIG. 7 is an image from a Western immunoblot for E2F3 and Rb expression in HCT-116 (wt-p53) cells transfected with non-specific miR, DHFR siRNA or miR-192.

The expression of miR-192 on the expression of E2F3 and Rb in HCT-116 (wt-p53) cells was also analyzed. In these experiments, HVT-116 (wt-p53) cells, as described above (see Example 3) were transfected with non-specific miR (FIG. 7, lane 2), DHFR siRNA (FIG. 7, lane 3) or miR-192 (FIG. 7, lane 4) according to the procedure described above (see Examples 1 and 2). One HCT-116 (wt-p53) sample was not transfected, and used as a negative control (FIG. 7, lane 1). Western immunoblot analysis was performed according to the procedure described above (see Example 5), except that rabbit anti-E2F-3 polyclonal antibody (1:1000, C-18) (Santa Cruz Biotechnology) was used.

The results (FIG. 7) indicated that miR-192 caused a decreased expression of E2F3 and Rb (FIG. 7, lane 4). The results further confirmed the notion that the function of miR-192 is clearly dependent on the status of wild type p53. It has been well characterized that the induction of the p53 dependent cell cycle check point control gene p21 is the key to trigger cell cycle arrest at both the G1 and G2 phase. The expression of the proapoptotic protein Bax was not altered, suggesting that the reduced proliferation may not be due to increased apoptosis. miR-192 overexpression also caused a slight decrease in the expression of E2F3 and Rb (FIG. 7), some of the key regulators of the G2/M transition. The decreased expression of E2F3 and Rb may be partially responsible for both the G1/S and G2/M arrest caused by miR-192 overexpression.

Example 7

With over-expression of miR-192 by transfection, both HCT-116 (wt-p53) and RKO (wt-p53) cells undergo cell cycle arrest at the G1 and G2 phase leading to decreased cellular proliferation. Bioinformatic analysis also reveals that there is a putative p53 binding site in the miR-192 promoter region.

To confirm this direct regulatory relationship, the following experiments were performed. First, the expression of the p53 protein was induced by treatment with MTX in HCT-116 (wt-p53) cells, RKO (wt-p53) cells, HCT-116 (null-p53) cells and HT-29 (mut-p53) cells (see Examples 1 and 2 for description of cell lines). Western immunoblot using mouse anti-p53 mAb (1:1000, DO-1) (Santa Cruz Biotechnology) according to the procedure discussed in Example 4 demonstrated that MTX treatment induced p53 protein expression (FIG. 8A).

Thereafter, the expression of endogenous mature miR-192 was analyzed by real time qRT-PCT analysis using an internal control RNU6B as an internal standard for normalization. The cDNA synthesis was carried out with the High Capacity cDNA synthesis kit (Applied Biosystems) using 10 ng of total RNA as template. The miRNA sequence-specific RT-PCR primers for miR-192 and endogenous control RNU6B were purchased from Ambion. Real-time quantitative reverse transcription-PCR (qRT-PCR) analysis was carried out using Applied Biosystems 7500 Real-Time PCR System. The PCR master mix containing TaqMan 2× Universal PCR Master Mix (No Amperase UNG), 10× TaqMan assay and RT products in 20 µl volume were processed as follows: 95° C. for 10 minutes, and then 95° C. for 15 seconds, 60° C. for 60 seconds for up to 40 cycles (n=3). Signal was collected at the endpoint of every cycle. The gene expression $\Delta C_T$ values of miRNAs from each sample were calculated by normalizing with internal control RNU6B and relative quantitation values were plotted.

Figure 8:
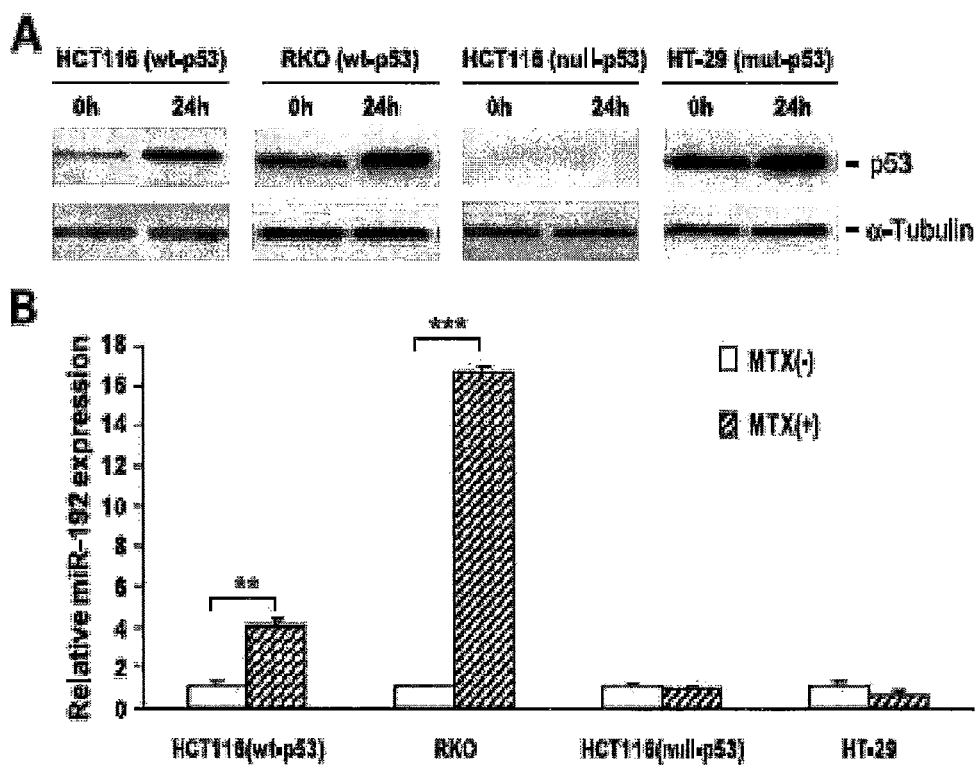
FIG. 8A is an image from a Western immunoblot for p53 expression in HCT-116 (wt-p53) cells, RKO (wt-p53) cells, HCT-116 (null-p53) cells and HT-29 cells after treatment with MTX.
FIG. 8B is a graph depicting the expression of endogenous mature miR-192 in HCT-116 (wt-p53) cells, RKO (wt-p53) cells, HCT-116 (null-p53) cells and HT-29 cells after treatment with MTX.

The results are illustrated in FIG. 8B where an open bar indicates an MTX(−) sample, and a dashed bar indicates an MTX(+) sample. The qRT-PCT (FIG. 8B) shows that induction of p53 by MTX caused a significant increase of miR-192 expression. By contrast, MTX treatment in HCT-116 (null-p53) and HT-29 (mut-p53) cells did not cause any change in the expression of miR-192 (FIG. 8B). These results suggest that the endogenous expression of miR-192 depends on the wild type p53.

Example 8

The promoter site of miR-192 contains a well conserved p53 binding sequence. FIG. 9A is a schematic diagram showing the position of the miR-192 promoter (over 3 kb) relative to the location of the miR-192 precursor on chromosome 11. To experimentally confirm a direct interaction between the p53 protein and the miR-192 promoter, chromatin immunoprecipitation-qRT-PCT (ChIP-qPCR) analysis was used to isolate p53-bound chromosome DNA. p21, a known cell cycle regulator transcriptionally regulated by p53, was used as a positive control. Mouse monoclonal antibody (DO-1) against p53 (Santa Cruz Biotechnology) was used for immunoprecipitation of the p53 binding complex. Non-related antibody α-tubulin (TU-02, Santa Cruz Biotechnology) was used as a negative control. Immunoprecipitation was performed based on the manufacturer's protocols of Active Motif. The primer sequences for the miR-192 promoter and the p21 promoter are listed as follows:

```
miR-192 promoter (forward primer):
5'-AGCACCTCCCATGTCACC-3'           (SEQ ID NO: 4)

miR-192 promoter (reverse primer):
5'-CAAGGCAGAGCCAGAGC-3'            (SEQ ID NO: 5)

p21 promoter (forward primer):
5'-GCTGGTGGCTATTTTGTCCTTGGGC-3'    (SEQ ID NO: 6)

p21 promoter (reverse primer):
5'-AGAATCTGACTCCCAGCACACACTC-3'    (SEQ ID NO: 7)
```

The isolated p53 specific binding DNA was PCR amplified using primers which span the predicted p53 binding sites of the miR-192 promoter or the positive control p21 promoter transcriptionally regulated by p53 protein.

Figure 9:
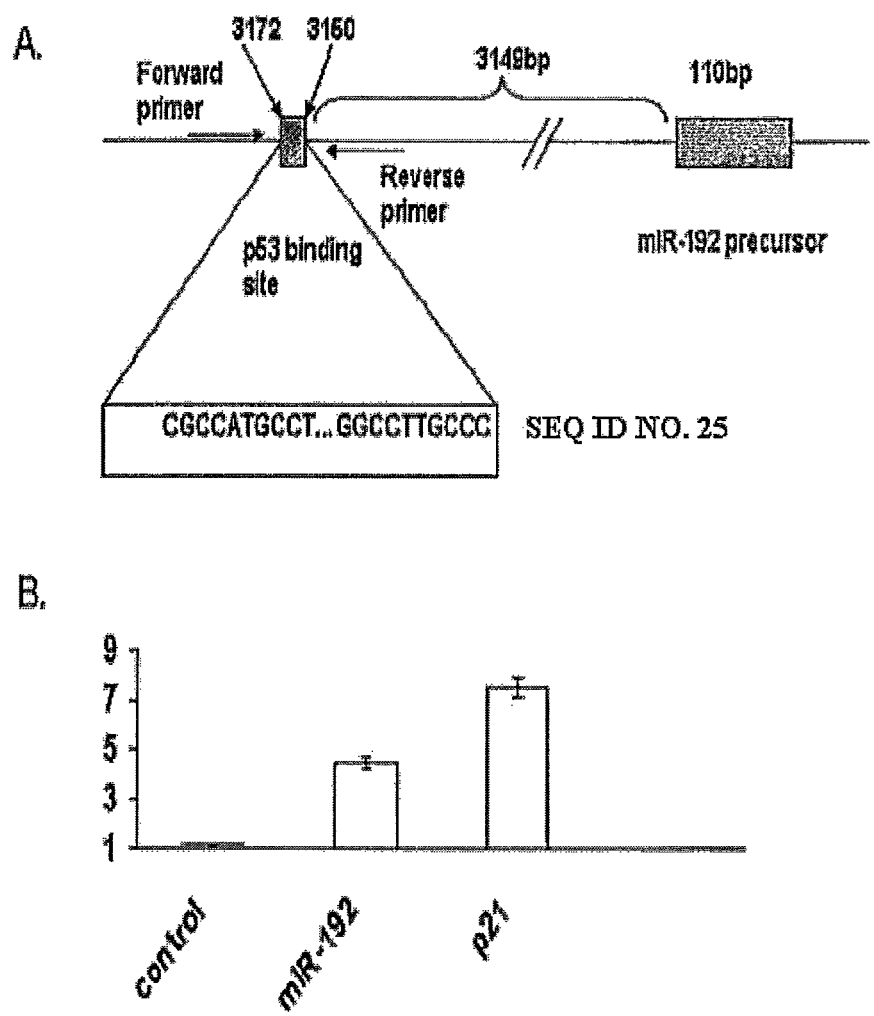
FIG. 9A is a diagram of miR-192 p53 binding site relative to miR-192 on chromosome 11.
FIG. 9B is a graph illustrating the immunoprecipitation qPCR analysis using chromosome DNA isolated with non-specific α-tubulin, p53 monoclonal antibody for the conserved p53 binding site located on the miR-192 or p21 promoter.

FIG. 9 shows the immunoprecipitation qPCR analysis of the predicted miR-192 promoter with conserved p53 binding sequence. FIG. 9B shows that the p53 protein directly interacts with the miR-192 promoter based on ChIP-qPCR analysis with a 4-old enriched, signal of with p53 specific monoclonal antibody compared to the non-specific antibody control DNA. This data establishes the existence of a conserved p53 binding site at the promoter region of miR-192. The binding sequence is 5'-gccatgcctxxxggccttgccc-3' (SEQ ID NO:25), with a 3-base-pair gap represented by "x". This suggests that miR-192, like miR-34, is another miRNA that is involved in the p53 tumor suppressor network.

Luciferase reporter assay was used to determine the transcriptional activation of conserved p53-binding promoter of miR-192. pGL3-Basic promoterless luciferase reporter plasmid (Promega) was used in this study. Double-stranded DNA oligonucleotides of conserved p53-binding sequence of miR-192 was synthesized and annealed and cloned upstream of firefly luciferase in the pGL3-Basic plasmid (miR-192-pGL3). The p53-binding site oligonucleotide (bold) contains MluI at the 5'-end and BglII sequence at the 3'-end (5'-ACGCGTCCCATGTCACCAC-CAGGGGTCGCCATGCCTCCTGGCCTTGC-CCAGCAAG ATCT-3') (SEQ ID NO:8). Control vector and miR-192-pGL3 vector were transfected into both HCT-116 (wt-p53) and HCT-116 (null-p53) cells. To further induce p53 expression, transfected HCT-116 (wt-p53) and HCT-116 (null-p53) cells were also treated with 5 µmol/L 5-fluorouracil for 24 hours. The promoter activity of each construct was quantified by dual luciferase assay (Promega) 24 hours after transfection. Firefly luciferase temperature for 1 hour. The primary antibodies used for the analysis included mouse anti-DHFR monoclonal antibody (mAb; 1:250) (BD Biosciences), mouse anti-p53 mAb (1:1,000; DO-1) (Santa Cruz Biotechnology), mouse antip21 mAb (1:1,000; F-5) (Santa Cruz Biotechnology), and mouse anti-α-tubulin mAb (1:1, 000; TU-02) (Santa Cruz Biotechnology). Horseradish peroxidase-conjugated antibodies against mouse or rabbit (1:1, 000) (Santa Cruz Biotechnology) were used as the secondary antibodies. Protein bands were visualized with a chemiluminescence detection system using the Super Signal substrate.

The conserved p-53 binding site at the promoter region of miR-192 can activate luciferase expression only in HCT-116 (wt-p53) cells. The activation was further enhanced by induced p53 expression in HCT (wt-p53) cells treated with 5-fluorouracil. By contrast, the induction of luciferase activity was completely absent from the HCT-116 (null-p53) cells. This evidences that miR-192, like miR-34, is another miRNA that is involved in the p53 tumor suppressor network.

p53 is one of the most frequent altered tumor suppressor gene in colorectal cancer. The potential function of multiple miRNAs involved in p53 tumor suppressor network is to provide the p53 with greater flexibility in rapidly responding to different growth condition changes, by perhaps having unique miRNAs (e.g. miR-34, miR-192) mediate the regulation of the key mRNA targets. miR-192 was one of the miRNAs with reduced expression in a large cohort of colon cancer patient samples, further supporting the potential impact and clinical relevance of miR-192 in colon cancer. The decrease or loss of the suppressive function of miR-192 in colon cancer may be an important factor related to cell cycle control and chemosensitivity to anti-folate based therapy.

Example 1-8 establish that miR-192 is directly involved in the regulation of a key anticancer target DHFR. The expression and function of the miR-192 is largely dependent on the presence of functional wild type p53. Thus, miR-192 may be used as a novel therapeutic option for treating cancer via an effective delivery system either alone or in combination with anti-folate compounds.

Example 9 miR-215 inhibits cell proliferation of HCT-116(wt-p53) and U-2 OS cells. HCT-116 (wt-p53), HCT-116 (null-p53), U-2 OS, and MG63 cells ($2 \times 10^5$) were plated in six-well plates, and transfected with 100 nM of either miR-215, miR-192 precursors or non-specific control miRNA (Ambion) after 24 h by Oligofectamine (Invitrogen) according to the manufacturer's protocols. siRNA specific to TS (Mishra, et al., "AmiR-24 microRNA binding site polymorphism in dihydrofolate reductase gene leads to methotrexate resistance," Prof Nat'l. Acad. Sci. (2007) 104:13513-13518) and siRNA specific to DHFR(ON -TARGET plus SMARTpool L-008799-00-0010, human DHFR, NM_000791) were purchased from Dharmacon and transfected with Oligofectamine (Invitrogen) at a final concentration of 100 nM. siRNA specific to TS or DHFR were used as the positive controls. miR-192, an miRNA that targets DHFR, was also used as the positive control.

Total RNA, including miRNA, was isolated from cell lines at 24 h after transfection, or from Stem cell lines or snap frozen tissues by using TRIzol reagent (Invitrogen) according to the manufacturer's instructions.

Real-time qRT-PCR confirmed the increased expression of miR-215 in the transfected cells. cDNA synthesis was carried out with the High Capacity cDNA synthesis kit (Applied Biosystems) using 10 ng of total RNA as template. The miRNA sequence-specific RT-PCR primers for miR-215 and endogenous control RNU6B were purchased from Ambion. Real-time quantitative reverse transcription-PCR (qRT-PCR) analysis was carried out using Applied Biosystems 7500 Real-Time PCR System. The PCR master mix containing TaqMan 2 Universal PCR Master Mix (No Amperase UNG), 10 TaqMan assay and RT products in 20 µl volume were processed as follows: 95° C. for 10 min, and then 95° C. for 15 sec, 60° C. for 60 sec for up to 40 cycles (n=3). Signal was collected at the endpoint of every cycle. The gene expression $\Delta C_T$ values of miRNAs from each sample were calculated by normalizing with internal control RNU6B and relative quantitation values were plotted.

Figure 10:
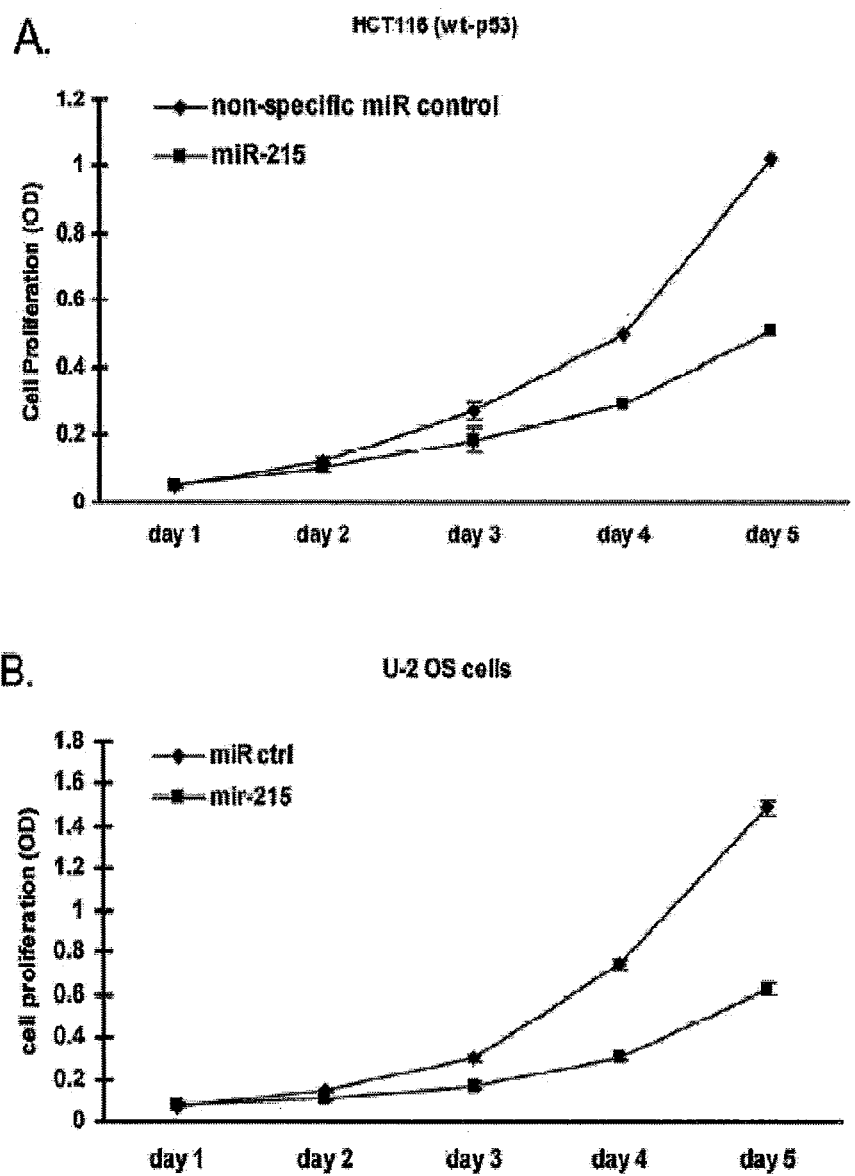
FIG. 10 shows inhibition of cell proliferation in either HCT-116 (wt-p53) (Panel A) or U-2 OS (Panel B) cells transfected with miR-215 precursors, i.e., a longer piece of miRNA (72 bps) with hairpin stem loop structure that is further processed by DICER to mature miRNA, compared with a non-specific miRNA control. The reduction in OD for cultures of HCT-116 (wt-p53) or U-2 OS cells were approximately 40% or 58% at day 5 respectively.

Cell proliferation assays were performed on the transduced cells. HCT-116 (wt-p53), HCT-116 (null-p53), U-2 OS, and MG63 cells were plated in 96-well plates in triplicate at $1 \times 10^3$ cells/well after transfection with miR-215 precursor or non-specific control miRNA. Cells were cultured for 24, 48, 72, 96 h. The absorbance at 450 and 630 nm was measured after incubation with 10 µl of WST-1 for 2 h. A remarkable inhibition of cell proliferation was observed in either HCT-116 (wt-p53) or U-2 OS cells compared with the non-specific miRNA control, and the reduction in HCT-116 (wt-p53) or U-2 OS cells were approximately 40% or 58% at day 5 respectively (FIG. 10).

miR-215 induces G2-arrest in HCT-116 (wt-p53) and U-2 OS cells. To investigate the mechanism by which miR-215 suppressed cell proliferation in HCT-116 (wt-p53) and U-2 OS cells, the impact of miR-215 on cell cycle control was analyzed by flow cytometry at 36 h after transfection. HCT-116 (wt-p53), HCT-116 (null-p53), U-2 OS and MG63 cells were transfected with miR-215 precursor and the non-specific control miRNA described as above. At 36 h after transfection, cells were harvested and resuspended at 0.5-1 $\times 10^5$ cells/ml in modified Krishan buffer containing 0.1% sodium citrate and 0.3% NP-40 and kept at 4° C. Before analysis by flow cytometry, cells were treated with 0.02 mg/ml RNase H and stained with 0.05 mg/ml propidium iodide (Sigma).

In miR-215 transduced U-2 OS cells, the proportion of cells in the G2-phase was higher and the proportion of cells in the S-phase was lower than that in control cells (18.50% vs 29.69%; 52.08% vs 41.24%; FIG. 11). The G2/S ratio was increased in miR-215 transfected cells (0.35 vs 0.72; >2-fold). The results showed that miR-215 causes increased accumulation of cells at G2-phase, whereas cells in S-phase decrease. Similar results were observed in transfected HCT-116 (wt-p53) cells.

miR-215 increases the expression of cell cycle control genes p53 and p21. p53 and p21, a downstream target of the p53 pathway of growth control, are reported to block cells at G2 checkpoint mainly through inhibiting activity of Cdc2, the cyclin-dependent kinase that normally drives cells into mitosis, which is the ultimate target of pathways that mediate rapid arrest in G2 in response to DNA damage. To further analyze the mechanism of cell proliferation inhibition by miR-215, we transfected miR-215 precursor into HCT-116 (wt-p53) and U-2 OS cells, and evaluated the levels of cell cycle control genes p53 and p21 by western immunoblot analysis.

At 48 h after transfection with miR-215, miR-192 precursors or non-specific control miRNA, the cells were scraped and lysed in RIPA buffer (Sigma). Equal amounts of proteins were resolved by SDS-PAGE on 12% gels by the method of Laemmli, and transferred to polyvinylidene fluoride membranes (BIO-RAD Laboratories). The membranes were then blocked by 5% nonfat milk in TBS-T (Tris-buffered saline and 0.5% Tween-20) at room temperature for 1 h. The primary antibodies used for the analysis included mouse anti-TS mAb (1:400, Millipore), mouse anti-DHFR mAb (1:250, BD Bioscience), mouse anti-p53 mAb (1:1000, DO-1), mouse anti-p21 mAb (1:1000, F-5), and mouse anti-α-tubulin mAb (1:1000, TU-02) purchased from Santa Cruz Biotechnology. Horseradish peroxidase—conjugated antibodies against mouse (1:1000, Santa Cruz Biotechnology) were used as the secondary antibodies. Protein bands were visualized with a chemiluminescence detection system using the Super Signal substrate (BIO-RAD).

Over-expression of miR-215 led to a significant increase of the p53 and p21 protein in both HCT-116 (wt-p53) and U-2 OS cells. (FIG. 12). The results indicated that miR-215 contributed to the inhibition of cell proliferation at least partially by the induction of G2-arrest in HCT-116(wt-p53) and U-2 OS cells through over-expression of G2-checkpoint genes p53 and p21.

Example 10

DHFR and TS are the direct targets of miR-215. Using the Sanger database (microrna.sanger.ac.uk) TS and DHFR were identified as putative targets of miR-215 (FIG. 13). At 48 hours after transfection, proteins were extracted from miR-215-transfected cells and from control cells and changes in TS or DHFR protein levels were determined by western immunoblot analysis (FIG. 14). Oligofectamine alone and non-specific miRNA were used as the negative controls. miR-192, which had been observed to down-regulate DHFR, was used as a positive control of DHFR down-regulation. Over-expression of miR-192 and miR-215 was confirmed by real time qRT-PCR analysis using U6 RNA to normalize the expression. Introduction of miR-192 or miR-215 clearly decreased TS or DHFR protein levels (FIG. 14, lane 3 and 4). Expression levels of TS or DHFR mRNA were analyzed using real time qRT-PCR analysis (FIG. 15). The results indicated that there was no reduction in TS or DHFR mRNA expression by miR-215 (column 3) and miR-192 (column 4). Thus, the suppression of TS or DHFR expression was regulated at the translational level without the degradation of TS or DHFR mRNA.

To confirm whether miR-215 directly targets TS or DHFR, plasmids were constructed containing the fragments of the 3'UTR of TS or DHFR in the downstream region of firefly luciferase. The pMIR-REPORT Luciferase miRNA Expression Reporter Vector (Ambion) was used to determine the targets of miR-215. Double stranded DNA oligonucleotides containing the miR-215 binding sequence (wt-miR-215) or mismatch sequence (mut-miR-215) in 3'UTR of TS or DHFR mRNA and the HindIII and SpeI restriction site overhangs were synthesized (IDT, Coralville, Iowa) and annealed and cloned downstream of firefly luciferase in the pMIR-REPORT plasmid. The sequences of these synthesized oligonucleotides are provided below. The 3'UTR of TS includes two miR-215 binding sites: one is located at 84-104 bp, one is located at 216-236 bp.

198-247 bp of 3'UTR of TS mRNA
Forward-wt-miR-215  5'-CTAGTAGTTAACTCCCTGAGGGT<u>ATCTGA</u>C<u>AATGC</u>TG<u>AGGTTAT</u>GAACAAAGTGA-3'
(SEQ ID NO: 14)

Reverse-wt-miR-215  5'-AGCTTCACTTTGTTCATAACCTCAGCATTGTCAGATACCCTCAGGGAGTTAACTA-3'
(SEQ ID NO: 15)

Forward-mut-miR-215  5'-CTAGTAGTTAACTCCCTGAGGGT<u>ATATCAC</u>GATG<u>T</u>TG<u>ATATCAC</u>GAACAAAGTGA-3'
(SEQ ID NO: 16)

Reverse-mut-miR-215  5'-AGCTTCACTTTGTTCGTGATATCAACATCGTGATATACCCTCAGGGAGTTAACTA-3'
(SEQ ID NO: 17)

62-115 bp of 3'UTR of TS mRNA
Forward-wt-miR-215-2  5'-CTAGTAGTTCTTTTTGCTCTAAAAGAAAAAGGAAC<u>TAGGTCAAAAA</u>TCTGTCCGA-3'
(SEQ ID NO: 18)

Reverse-wt-miR-215-2  5'-AGCTTCGGACAGATTTTTGACCTAGTTCCTTTTTCTTTTAGAGCAAAAAGAACTA-3'
(SEQ ID NO: 19)

519-578 bp of 3'UTR of DHFR mRNA
Forward-wt-miR-215  5'-CTAGTAATTTCAGTGAAAGCAGTGT<u>ATTTGCTAGG</u>TCATACCAGAAATCATCAATTGAGGTACGGA-3'
(SEQ ID NO: 20)

Reverse-wt-miR-215  5'-AGCTTCCGTACCTCAATTGATGATTTCTGGTATGACCTAGCAAATACACTGCTTTCACTGAAATTA-3'
(SEQ ID NO: 21)

Forward-mut-miR-215  5'-CTAGTAATTTCAGTGAAAGCAGTGT<u>GCTTGCGATA</u>TGATACCAGAAATCATCAATTGAGGTACGGA-3'
(SEQ ID NO: 22)

Reverse-mut-miR-215  5'-AGCTTCCGTACCTCAATTGATGATTTCTGGTATCATATCGCAAGCACACTGCTTTCACTGAAATTA-3'
(SEQ ID NO: 23)

The constructs were transiently transfected into HCT-116 (wt-p53) cells alone (control) or together with miR-215 precursor. Twenty-four hours before transfection, HCT116 (wt-p53) and HCT 116 (null-p53) cells were plated in the 96-well plates at 1.5×10⁴ cells each well in triplicate. pMIR-REPORT constructs (100 ng) together with 1 ng of Renilla luciferase plasmid phRL-SV40 (Promega, Madison, Wis.) were transfected by Lipofectamine 2000 (Invitrogen, Carlsbad, Calif.) according to the protocols provided by the manufacturer. Thirty hours after transfection, cells were lysated and luciferase activity was measured by the dual-luciferase reporter assay system (Promega, Madison, Wis.) according to the instructions. Firefly luciferase activity for each condition was normalized by dividing to Renilla internal control and then compared to pMIR-REPORT.

Figure 16:
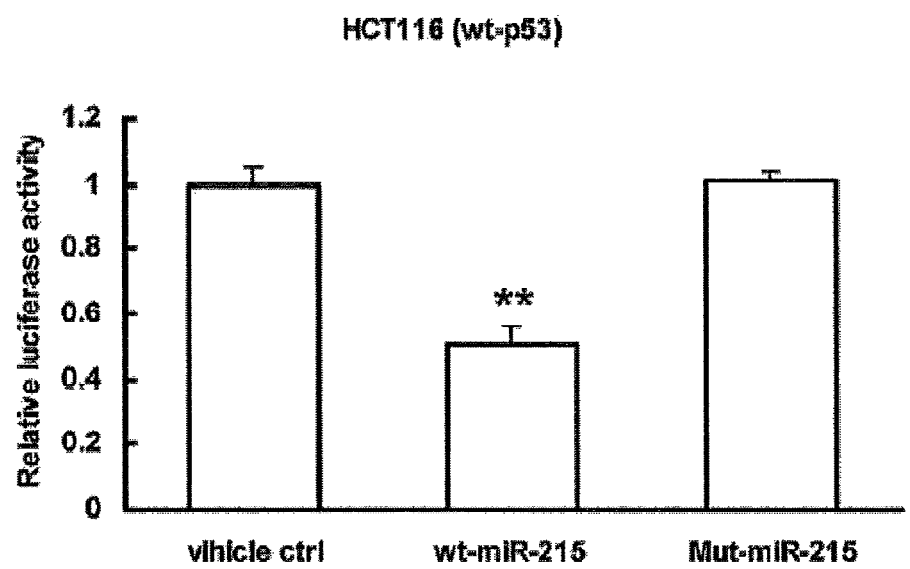
FIG. 16 depicts the level of luciferase reporter activity from a construct containing the 3' UTR binding sequence for miR-215 (or a mutated binding sequence) in response to transfection with miR-215.

As shown in FIG. 16, there was a significant decrease of luciferase activity compared to the vector alone. These data demonstrated that TS or DHFR were the direct targets of miR-215, and suggested that the inhibition of cell proliferation by miR-215 was partially due to the down-regulation of these two enzymes.

Example 11

Reduced chemosensitivity to TDX and MTX by overexpression of miR-215. TS and DHFR are the major targets of cancer chemotherapy in the clinic. TDX, the third-generation TS inhibitor, is an active agent in the treatment of human colon and breast cancer. Inhibitors of DHFR, such as MTX, are widely used in the treatment of human leukemia, osteosarcoma and choriocarcinoma. Increased DHFR protein levels are reported to be associated with drug resistance, and low tumor expression levels of TS have also been linked with improved outcome for colon cancer patients treated with 5-FU chemotherapy. However, Yamauchi et al observed that MTX has the highest activity at the time when DNA synthesis, DHFR activity, DHFR content, and DHFR mRNA content increased and the lowest activity at the time when they decreased.

In this study, we confirmed miR-215 decreased the expression of TS and DHFR protein, we then test if miR-215 can change the sensitivity of TDX or MTX in the HCT-116 (wt-p53) or U-2 OS cells.

HCT-116 (wt-p53) cells were plated in 96-well plates at 1×10³ cells/well in triplicate and were transfected with miR-215 precursor, non-specific control miRNA, or siRNA against TS or DHFR in 100 µl of medium. Twenty-four hours later, TDX or MTX in 100 µl medium ranged from 10-200 nM was added, and incubated for 72 hours. To measure viable cells, 10 µl of WST-1 (Roche Applied Science) was added to each well. After 2 hours incubation, absorbance was measured at 450 and 630 nm respectively (n=3). Non-specific control miRNA alone was used as a negative control, and siRNAs incubation with TDX or MTX were used as the positive controls.

FIG. 17A shows that the $IC_{50}$ of TDX in HCT-116(wt-p53) cells transfected with miR-215 was 98.7 nM, whereas in the negative control was 18.6 nM, in the positive control was 8.5 nM. FIG. 8B showed that 83.6% of transduced U-2 OS cells still alive at 200 nM of MTX. The $IC_{50}$ of MTX in the negative control was 49.7 nM, whereas 37.3 nM in the positive control. These results indicated that down-regulation of TS or DHFR protein by the siRNA specific against TS or DHFR indeed increased the sensitivity of TDX or MTX in the colon cancer or osteosarcoma cell lines, whereas even though miR-215 also down-regulated the expression levels of TS or DHFR, it did not increase the chemosensitivity of TDX or MTX compared to the non-specific miRNA control. TDX or MTX are considered to be more effective on the cells in the S-phase. The cell cycle data showed that siRNAs specific against TS or DHFR did not decrease the cells in the S-phase (FIG. 11), whereas the cells in the S-phase were reduced in the miR-215 transfected cells.

Figure 18:
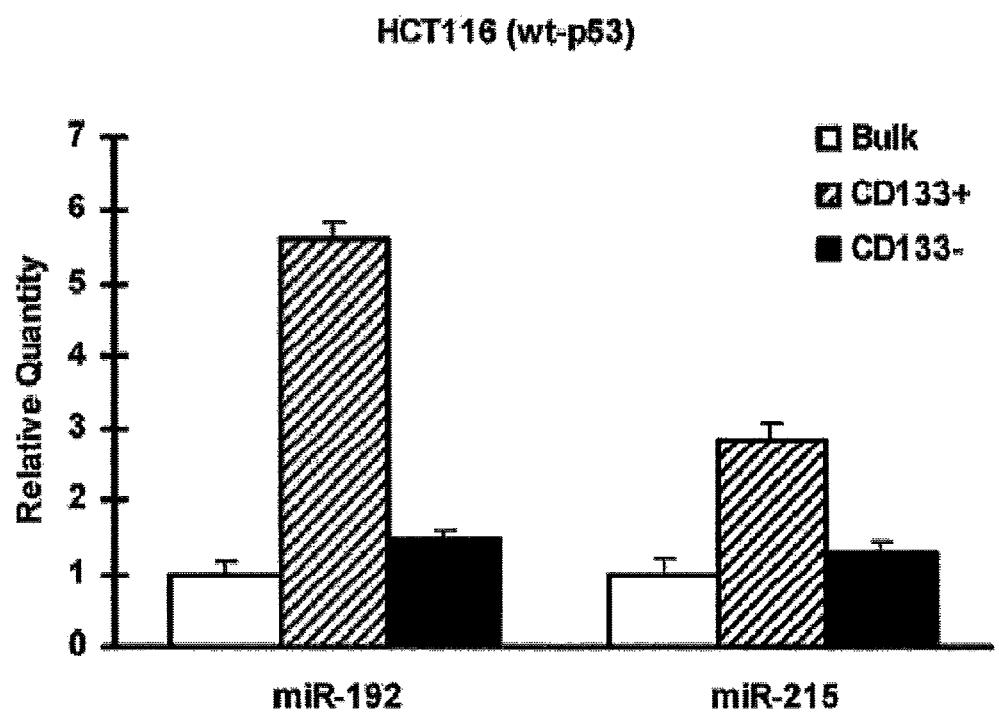
FIG. 18 depicts miR-192 and miR-215 expression in CD133$^+$ HCT-116 (wt-p53) cells as compared to CD133$^-$ cells.

Over-expression of miR-215 in human colon cancer stem cells may contribute to the low sensitivity to TDX and MTX. Cancer stem cells also named cancer initiating cells, exhibit low rate of division and proliferation in their niche that help them to avoid chemotherapy and radiation. To determine whether miR-215 expression influences the growth and chemosensitivity in cancer stem cells, miR-215 levels in colon cancer stem cells were measured using real-time qRT-PCR. Expression of miR-215 was determined to be greater than 2-fold higher in the colon cancer stem cells than in the controls (FIG. 18).

Example 12

Figure 19:
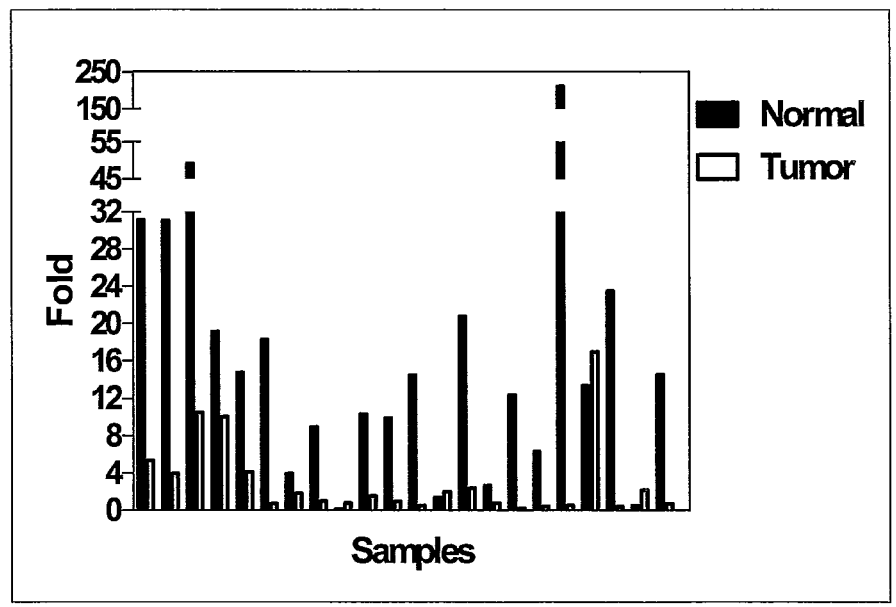
FIG. 19 depicts miR-215 expression in paired human colon cancer and counterpart normal tissues.
Figure 19:
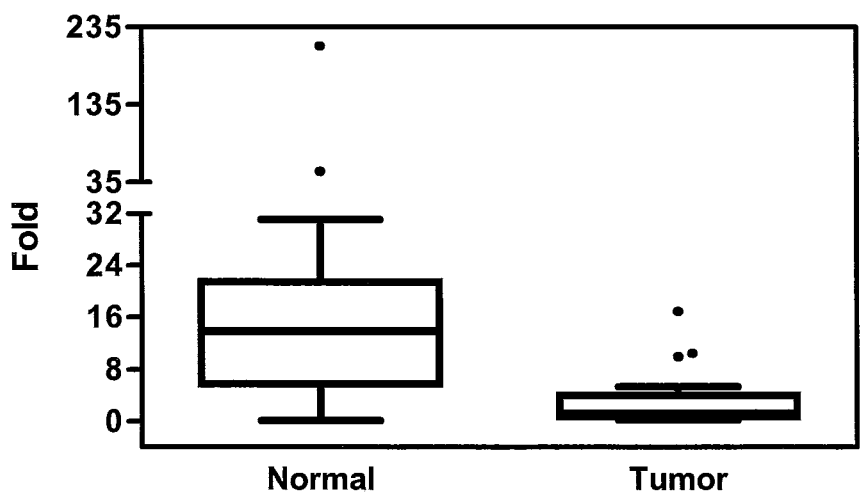

Clinical human colon cancers show decreased miR-215 expression. miR-215 expression in 22 paired human colon cancer and counterpart normal tissues was analyzed by real-time qRT-PCR (FIG. 19). Eighteen of 22 colon cancer samples (81.8%) showed decreased miR-215 level (P<0.05).

From the description and examples provided above, one of ordinary skill in the art would appreciate the application of miR-192 and miR-215 in various diagnostic tools and treatments.

Example 13

It is contemplated that miR-192 and miR-215 would be altered in a subject simultaneously according to the methods discussed above, or that the inhibitory molecule would comprise a combination of miR-192 and miR-215. When both are altered, it is expected that there would be greater than the effect observed with either miR-192 or miR-215, or would have a synergistic effect. For example, it is expected that if miR-192 and miR-215 are both inhibited in a subject, then the sensitivity to a chemotherapeutic agent would be increased, and that this increase would be greater than the increase in sensitivity observed with miR-192 or miR-215. It is further expected that if miR-192 and miR-215 are upregulated together, then the decrease in cell proliferation would be greater than observed with miR-192 or miR-215.

What is claimed is:

1. A method of increasing sensitivity of a cell to a chemotherapeutic agent, comprising contacting the cell with a nucleic acid selected from the group consisting of a complimentary sequence to SEQ ID NOs:1, 2, 3, 9, 10 and 25 or having a sequence of SEQ ID NO:25, in an amount effective to sensitize the cell to the chemotherapeutic agent, wherein the sensitivity of the cell to the chemotherapeutic agent is increased, and contacting the cell with the chemotherapeutic agent.

2. The method of claim 1, wherein the chemotherapeutic agent is selected from methotrexate, fluorouracil (5-FU), and ralitrexed.

3. The method of claim 1, wherein the nucleic acid is an antisense nucleic acid.

4. The method of claim 1, wherein the nucleic acid is an siRNA or an shRNA.

5. The method of claim 1, wherein the cell is a cancer stem cell.

6. The method of claim 1, wherein the cell is a neoplastic cell.

* * * * *

UNITED STATES PATENT AND TRADEMARK OFFICE
CERTIFICATE OF CORRECTION

PATENT NO. : 8,927,207 B2
APPLICATION NO. : 12/996249
DATED : January 6, 2015
INVENTOR(S) : Jingfang Ju et al.

It is certified that error appears in the above-identified patent and that said Letters Patent is hereby corrected as shown below:

On the Title Page, item 56

Page 2, Column 1, OTHER PUBLICATIONS, Line 21, delete "noval" and insert -- novel --

Page 2, Column 1, OTHER PUBLICATIONS, Line 59, delete "Neoplasis" and insert -- Neoplasia --

Page 3, Column 2, OTHER PUBLICATIONS, Line 13, delete "tymidine" and insert -- thymidine --

Signed and Sealed this
Fifth Day of May, 2015

Michelle K. Lee
*Director of the United States Patent and Trademark Office*